(12) United States Patent
Kuo

(10) Patent No.: US 7,029,681 B2
(45) Date of Patent: *Apr. 18, 2006

(54) MULTIPLE AND MULTIVALENT DNA VACCINES IN OVO

(75) Inventor: Tsun Yung Kuo, I-Lan (TW)

(73) Assignee: Schweitzer Chemical Corporation, City of Industry, CA (US)

(*) Notice: Subject to any disclaimer, the term of this patent is extended or adjusted under 35 U.S.C. 154(b) by 218 days.

This patent is subject to a terminal disclaimer.

(21) Appl. No.: 10/377,718

(22) Filed: Mar. 4, 2003

(65) Prior Publication Data

US 2003/0175291 A1 Sep. 18, 2003

Related U.S. Application Data

(60) Provisional application No. 60/362,547, filed on Mar. 8, 2002.

(51) Int. Cl.
*A61K 39/295* (2006.01)
*A61K 31/7088* (2006.01)

(52) U.S. Cl. .................. 424/199.1; 514/44; 424/202.1

(58) Field of Classification Search .................. 514/44; 424/199.1, 202.1; 536/23.72; 435/91.41, 435/320.1
See application file for complete search history.

(56) References Cited

U.S. PATENT DOCUMENTS

| | | | |
|---|---|---|---|
| 4,458,630 A | 7/1984 | Sharma et al. | |
| 5,056,464 A | 10/1991 | Lewis | |
| 5,397,568 A | 3/1995 | Whitfill et al. | |
| 5,397,569 A | 3/1995 | Whitfill et al. | |
| 5,595,912 A | 1/1997 | Vakharia et al. | |
| 5,643,578 A | 7/1997 | Robinson et al. | |
| 5,693,530 A | 12/1997 | Schat et al. | |
| 5,699,751 A | 12/1997 | Phelps et al. | |
| 5,750,101 A | 5/1998 | Stone | |
| 5,780,289 A | 7/1998 | Vermeulen et al. | |
| 5,817,320 A | 10/1998 | Stone | |
| 5,871,748 A | 2/1999 | Whitfill et al. | |
| 6,032,612 A | 3/2000 | Williams | |
| 6,048,535 A * | 4/2000 | Sharma .................. | 424/202.1 |
| 6,136,319 A | 10/2000 | Whitfill et al. | |
| 6,221,362 B1 * | 4/2001 | Audonnet et al. ....... | 424/199.1 |
| 6,286,455 B1 | 9/2001 | Williams | |
| 6,299,874 B1 | 10/2001 | Whitfill et al. | |
| 6,322,780 B1 | 11/2001 | Lee et al. | |

FOREIGN PATENT DOCUMENTS

| WO | WO 90/02802 | * | 3/1990 |
|---|---|---|---|
| WO | WO 98/03659 | * | 1/1998 |

OTHER PUBLICATIONS

Reddy et al (Vaccine 14:369-477, 1996).*
deLeeuw et al (Journal of General Virology 80:131-136, 1999).*
Kusters et al (Virology 169:217-221, 1989).*
Liu et al. Locus AF458480. Sep. 16, 2002. [online] [retrieved on Jul. 30, 2004] Retrieved from http://www.ncbi.nlm.nig.gov/entrez/viewer.fcgi?db=nucleotide&val=22901270.*
Liu et al. Locus AF458481. Sep. 16, 2002. [online] [retrieved on Jul. 30, 2004] Retrieved from http://www.ncbi.nlm.nih.gov/entrez/viewer.fcgi?db=nucleotide&val=22901272.*
Liu et al. Locus AF458482. Sep. 16, 2002. [online] [retrieved on Jul. 30, 2004] Retrieved from http://www.ncbi.nlm.nih.gov/entrez/viewer.fcgi?db=nucleotide&val=22901274.*
Isobe et al. Locus APFHENE4. Feb. 3, 1999. [online] [retrieved Jul. 30, 2004] Retrieved from http://www.ncbi.nlm.nih.gov/entrez/viewer.fcgi?db=nucleotide&val=221023.*
Bayliss et al (Journal of General Virology 71:1303-1312, 1990).*
Gagic,M. et al., "In Ovo Vaccination of Specific-pathogen-free Chickens with Vaccines Containing Multiple Agents", Avian Diseases. 1999, vol. 43, pp. 293-301.
Sharma, J.M., "Embryo Vaccination with infectious Bursal Disease Virus Alone or in Combination with Marek's Disease Vaccine", Avian Diseases. 1985, vol. 29 No. 4, pp. 1155-1169.
Sharma, J.M., "Embryo Vaccination of Specific-Pathogen-Free Chickens with Infectious Bursal Disease Virus: Tissue Distribution of the Vaccine Virus and Protection of Hatched Chickens against Disease", Avian Diseases. 1985, vol. 30 No. 4, pp. 776-780.
Reddy, S.K. et al., "Protective efficacy of a recombinant herpesvirus of turkeys as an in ovo vaccine against Newcastle and Marek's diseases in specific-pathogen-free chickens", Vaccine. 1996, vol. 14 No. 6, pp. 469-477.

* cited by examiner

*Primary Examiner*—Mary E. Mosher
(74) *Attorney, Agent, or Firm*—Fei-Fei Chao; Bingham McCutchen LLP

(57) ABSTRACT

The present invention provides a muliple DNA vaccine and/or a multivalent DNA vaccine for use in aquiring embroyonic immunity in fowl eggs. The multiple DNA vaccine contains two or more DNA constructs, each containing a DNA molecule encoding an avian viral protein or a fragment thereof capable of inducing a protective immune response against the avian viral disease in fowl. The multivalent DNA vaccine contains one DNA construct which contains two or more DNA molecules, each representing an avian viral gene or a fragment thereof. The multivalent DNA vaccine is capable of expressing two or more viral antigens and inducing protective immune responses against the avian viral diseases in fowl. Both the multiple DNA vaccine and the multivalent DNA vaccine are preferred to be injected into the amniotic fluid of the fowl egg after being fertilized for about 18 days.

26 Claims, No Drawings

MULTIPLE AND MULTIVALENT DNA VACCINES IN OVO

RELATED APPLICATION

This application claims the priority of U.S. Provisional Application Ser. No. 60/362,547, filed on Mar. 8, 2002, which is herein incorporated by reference.

FIELD OF THE INVENTION

The present invention relates to either a muliple DNA vaccine or a multivalent DNA vaccine for use in aquiring embroyonic immunity in fowl eggs and methods for preparing and using the same. The multiple DNA vaccine contains two or more DNA constructs, each containing a DNA molecule encoding an avian viral protein or a fragment thereof capable of inducing a protective immune response against an avian viral disease in fowl. The multivalent DNA vaccine contains a DNA construct which contains two or more DNA molecules. Each of the DNA molecules represents an avian viral gene or a fragment thereof. The multivalent DNA vaccine is capable of expressing two or more viral antigens and inducing protective immune responses against two or more of the avian viral diseases in fowl. Both the multiple DNA vaccine and the multivalent DNA vaccine are preferred to be injected into the amniotic fluid of the fowl egg after being fertilized for about 18 days.

BACKGROUND OF THE INVENTION

In ovo vaccination of virus-containing vaccines was extensively described by Sharma et al. (U.S. Pat. No. 4,458,630). In particular, it teaches that live Marek's disease virus can be injected into amniotic fluid within the egg, whereafter the embryo is infected and the vaccine virus replicates to a high titer which induces the formation of protective antibodies in the treated embryo. (See Sharma (1985), *Avian Diseases* 29, 1155, 1167–68).

It is well-known in the worldwide poultry business that certain viral diseases, such as Marek's disease virus (MDV), infectious bursal disease virus (IBDV), Newcastle disease virus (NDV), infectious bronchitis virus (IBV), infectious laryngotracheitis virus (ILTV), avian encephalomyelitis (AEV), chick anemia virus (CAV), Fowlpox virus (FPV), avian influenza virus (AIV), reovirus, avian leukosis virus (ALV), reticuloendotheliosis virus (REV), avian adenovirus and hemorrhagic enteritis virus (HEV), may cause major outbreak and result in significant economic losses in the commercial poultry industry. Among them, MDV, IBDV, NDV and IBV, are particularly important due to their virulent nature.

Marek's Disease (MD) is a malignant, lymphoproliferative disorder disease that occurs naturally in chickens. The disease is caused by a herpesvirus: Marek's Disease Virus (MDV). MD is ubiquitous, occurring in poultry-producing countries throughout the world. Chickens raised under intensive production systems will inevitably suffer losses from MD. The symptoms of MD appear widely in the nerves, genital organs, internal organs, eyes and skin of the infected birds, causing motor trouble (due to paralysis when the nerves have been affected), functional trouble of the internal organs (due to tumors), and chronic undernourishment (if the internal organs are attacked by the virus). MD affects chickens from about 6 weeks of age, occurring most frequently between ages of 12 and 24 weeks.

At of this time, there are no methods of treating MD. The control of the disease is based primarily on management methods such as insolating growing chickens from sources of infection, the use of genetically resistant stock, and vaccination. However, management procedures are normally not cost-effective and the progress has been disappointing with respect to the selection of poultry stock with increased genetically controlled resistance. Nowadays, control of MD is almost entirely based on vaccination.

Infectious bursal disease virus (IBDV) is responsible for a highly contagious immunosuppressive disease in young chickens which causes significant losses to the poultry industry worldwide (See Kibenge (1988), *J. Gen. Virol.*, 69:1757–1775). Infection of susceptible chickens with virulent IBDV strains can lead to a highly contagious immunosuppressive condition known as infectious bursal disease (IBD). Damage caused to the lymphoid follicles of the bursa of Fabricius and spleen can exacerbate infections caused by other agents and reduce a chicken's ability to respond to vaccination as well (See Cosgrove (1962), *Avian Dis.*, 6:385–3894).

IBDV is a member of the Birnaviridae family and its genome consists of two segments of double-stranded RNA (See Dobos et al (1979), *J. Virol.*, 32:593–605). The smaller segment B (about 2800 bp) encodes VP 1, the dsRNA polymerase. The larger genomic segment A (about 3000 bp) encodes a 110 kDa precursor polypeptide in a single open reading frame (ORF) that is processed into mature VP2, VP3 and VP4 (See Azad et al (1985), *Virology*, 143:35–44). From a small ORF partly overlapping with the polypeptide ORF, segment A can also encode VP5, a 17-kDa protein of unknown function (See Kib While VP2 and VP3 are the major structural proteins of the virion, VP2 is the major host-protective immunogen and causes induction of neutralizing antibodies (See Becht et al. (1988), *J. Gen. Virol.*, 69:631–640; Fahey et al. (1989), *J. Gen. Virol.*, 70:1473–1481). VP3 is considered to be a group-specific antigen because it is recognized by monoclonal antibodies (Mabs) directed against VP3 from strains of both serotype 1 and 2 (See Becht et al (1988), *J. Gen. Virol.*, 69:631–640). (See Jagadish et al. (1988), *J. Virol.*, 62:1084–1087).

In the past, control of IBDV infection in young chickens has been achieved by live vaccination with avirulent strains, or principally by the transfer of maternal antibody induced by the administration of live and killed IBDV vaccines to breeder hens. Unfortunately, in recent years, virulent variant strains of IBDV have been isolated from vaccinated flocks in the United States (See e.g., Snyder et al. (1988), *Avian Dis.*, 32:535–539; Van der Marel et al. (1990), *Dtsch. Tierarztl. Wschr.*, 97:81–83), which drastically undermine the effectiveness of using live vaccination for IBDV.

Efforts to develop a recombinant vaccine for IBDV have also been made, and the genome of IBDV has been cloned (See Azad et al (1985) "Virology", 143:35–44). The VP2 gene of IBDV has been cloned and expressed in yeast (See Macreadie et al. (1990), *Vaccine*, 8:549–552), as well as in recombinant fowlpox virus (See Bayliss et al (1991), *Arch. Virol.*, 120:193–205). When chickens were immunized with the VP2 antigen expressed from yeast, antisera afforded passive protection in chickens against IBDV infection. When used in active immunization studies, the fowlpox virus-vectored VP2 antigen afforded protection against mortality, but not against damage to the bursa of Fabricius.

Newcastle disease virus (NDV) is an enveloped virus containing a linear, single-strand, nonsegmented, negative sense RNA genome. Typically, virus families containing enveloped single-stranded RNA of the negative-sense genome are classified into groups having non-segmented genomes (e.g., Paramyxoviridae and Rhabdoviridae) or those having segmented genomes (e.g., Orthomyxoviridae, Bunyaviridae and Arenaviridae). NDV, together with parainfluenza virus, Sendai virus, simian virus 5, and mumps virus, belongs to the Paramyxoviridae family.

The structural elements of the NDV include the virus envelope which is a lipid bilayer derived from the cell plasma membrane. The glycoprotein, hemagglutinin-neuraminidase (HN) protrude from the envelope allowing the virus to contain both hemagglutinin and neuraminidase activities. The fusion glycoprotein (F), which also interacts with the viral membrane, is first produced as an inactive precursor, then cleaved post-translationally to produce two disulfide linked polypeptides. The active F protein is involved in penetration of NDV into host cells by facilitating fusion of the viral envelope with the host cell plasma membrane. The matrix protein (M), is involved with viral assembly, and interacts with both the viral membrane as well as the nucleocapsid proteins.

The main protein subunit of the NDV nucleocapsid is the nucleocapsid protein (NP) which confers helical symmetry on the capsid. In association with the nucleocapsid are the P and L proteins. The phosphoprotein (P), which is subject to phosphorylation, is thought to play a regulatory role in transcription, and may also be involved in methylation, phosphorylation and polyadenylation. The L gene, which encodes an RNA-dependent RNA polymerase, is required for viral RNA synthesis together with the P protein. The L protein, which takes up nearly half of the coding capacity of the viral genome is the largest of the viral proteins, and plays an important role in both transcription and replication.

The replication of all negative-strand RNA viruses, including NDV, is complicated by the absence of cellular machinery required to replicate RNA. Additionally, the negative-strand genome can not be translated directly into protein, but must first be transcribed into a positive-strand (mRNA) copy. Therefore, upon entry into a host cell, the virus can not synthesize the required RNA-dependent RNA polymerase. The L, P and NP proteins must enter the cell along with the genome on infection. Both the NDV negative strand genomes (vRNAs) and antigenomes (cRNAs) are encapsidated by nucleocapsid proteins; the only unencapsidated RNA species are virus mRNAs. The cytoplasm is the site of NDV viral RNA replication, just as it is the site for transcription. Assembly of the viral components appears to take place at the host cell plasma membrane and mature virus is released by budding.

In U.S. Pat. No. 5,427,791, Ahmad et al. describe the embryonal vaccination against NDV, which requires the modification of the viruses through the use of ethyl methane sulfonate (EMS). However, EMS is a mutagen so that the vaccine prepared by the use of EMS is suspected to act as a mutagen as well, which is undesirable for regular administration of the vaccine. Nevertheless, without the modification with EMS, the NDV vaccine cannot be applied for in ovo vaccination as almost all of the embryos will die upon injection of the eggs with the unmodified virus.

Infectious bronchitis virus (IBV), the prototype of the family Coronaviridae, is the etiological agent of infectious bronchitis (IB). The virus has a single-stranded RNA genome, approximately 20 kb in length, of positive polarity, and is usually about 80–100 nm in size, being round with projecting 20 nm spikes. IBV is the causative agent of an acute, highly contagious disease in chickens of all ages, affecting the respiratory, reproductive and renal systems.

IBV contains three structural proteins: the spike (S) glycoprotein, the membrane glycoprotein, and the nucleocapsid protein. The spike glycoprotein is so called because it is present in the teardrop-shaped surface projections or spikes protruding from the lipid membrane of the virus. The spike protein is believed likely to be responsible for immunogenicity of the virus, partly by analogy with the spike proteins of other corona-viruses and partly by in vitro neutralisation experiments (See, e.g., D. Cavanagh et al. (1984), *Avian Pathology*, 13, 573–583). There are two spike glycoproteins, which are S1 (90,000 daltons) and S2 (84,000 daltons). The polypeptide components of the glycopolypeptides S1 and S2 have been estimated after enzymatic removal of oligosaccharides to have a combined molecular weight of approximately 125,000 daltons. It appears that the spike protein is attached to the viral membrane by the S2 polypeptide.

IBV has been wide-spread in countries where an intensive poultry industry has been developed. Young chickens up to 4 weeks of age are most susceptible to IBV, infection leading to high rates of morbidity and to mortality resulting from secondary bacterial infection. Infection also results in a drop in egg production, or failure to lay at full potential, together with an increase in the number of down-graded eggs with thin, misshapen, rough and soft-shells produced, which can have a serious economic effect.

Administering live vaccines to a developing chick in the egg (in-ovo) has proven to be a fast (40,000 eggs per hour), effective (100% of the eggs receive the vaccine), and labor saving ($100,000 per year per hatchery) method to vaccinate baby chicks against certain diseases before they hatch.

The first in-ovo vaccination machine for use on chicken hatching eggs was developed by Embrex, Inc., of Raleigh, N.C. in the late 1980s. (See U.S. Pat. Nos. 5,056,464 and 5,699,751). This in-ovo machine is currently used in about 80% of the U.S. broiler hatcheries, primarily for administering MD vaccines. The popularity of this machine, which has proven to be safe and effective in vaccination of chicks against MD, is also being used increasingly to administer IBD vaccines and ND vaccines.

In the invention to be presented in the following sections, a DNA-mediated immunization (collectively "DNA vaccines") will be introduced. There are two kinds of DNA vaccines, i.e., a multiple DNA vaccine and a multivalent DNA vaccine. The multiple DNA vaccine of the present invention contains a combination of two or more DNA construct, each containing a single DNA molecule which is a viral gene or a fragment thereof. The multivalent DNA vaccine of the present invention contains two or more viral genes or fragments thereof linking together in one DNA construct. The viral genes or fragments used in preparation of either the multiple DNA vaccine or the multivalent DNA vaccine are those that encode viral peptides which are antigenic to and can induce both the humoral and the cellular immune system in a host. The DNA vaccines are preferably applied to the egg by needles. The injection of the DNA vaccines in ovo leads to surprisingly strong immune responses which include not only antibody induction and T-cell activation with cytokine secretion, but also the production of cytotoxic T lymphocytes (CTL).

SUMMARY OF THE INVENTION

The present invention provides a multiple DNA vaccine for in ovo injection. The multiple DNA vaccine contains two or more DNA constructs, each DNA construct expressing an antigenic protein of an avian virus causing avian viral disease in fowl. The antigenic protein of the avian virus is capable of inducing a protective immune response against an avian viral disease. The multiple DNA vaccine is preferred to inject into the egg, particularly the amniotic fluid of the egg, of the fowl. The egg is preferred to be fertilized for about 18 days. The preferred fowl includes chicken, turkey, duck, and goose.

The DNA construct contains a DNA molecule and a vector. The vector can be a plasmid or a viral carrier. The preferred vector is a plasmid. Examples of the plasmid include, but are not limited to, pcDNA3, pVAX1, pSectag, pTracer, pDisplay, pUC system plasmid (such as pUC7, pUC8, pUC18), and pGEM system plasmid. Alternatively, any plasmid which contains a promoter such as CMV promoter, SV40 promoter, RSV promoter, and β-actin promoter, can also be used for preparing the DNA construct. The most favorable plasmid is pcDNA3. The preferred viral carrier is one selected from the group consisting of a baculovirus, a herpes virus, and a pox virus.

Examples of the avian virus include, but are not limited to Marek's disease virus (MDV), infectious vursal disease virus (IBDV), Newcastle disease virus (NDV), infectious bronchitis virus (IBV), infectious laryngotracheitis virus (ILTV), avian encephalomyelitis (AEV), avian leukosis virus (ALV), fowlpox virus (FPV), avian paramyxovirus (APV), duck hepatitis virus (DHV), and hemorrhagic enteritis virus (HEV).

The DNA molecules that are particularly suitable for inducing a protective immune response against the avian viral diseases as shown above include, but are not limited to, the entire of gB gene of Merk's Disease virus (MDV) having the DNA sequence of SEQ ID NO:1 or a fragment thereof; the entire VP2 gene of infectious bursal disease virus (IBDV) having the DNA sequence of SEQ ID NO:2 or a fragment thereof; the entire HN gene of Newcastle disease virus (NDV) having the DNA sequence (which is from bases 6321 to 8319) of SEQ ID NO:3 or a fragment thereof (i.e., SEQ ID NO:3 is the entire genome of the NDV); the entire S1 gene of infectious bronchitis virus (IBV) having the DNA sequence of SEQ ID NO:4 or a fragment thereof; the entire glycoprotein G gene of infectious laryngotracheitis virus (ILTV) having the DNA sequence of SEQ ID NO:5 or a fragment thereof; the entire VP1, VP0, or VP3 gene of avian encephalomyelitis virus (AEV) or a fragment thereof (the VP1 gene has the DNA sequence of SEQ ID NO:6; the VP0 gene has the DNA sequence of SEQ ID NO:7; and the VP3 gene has the DNA sequence of SEQ ID NO:8); the entire paraglycoprotein G gene of avian parainfluenza virus (APV) having the DNA sequence of SEQ ID NO:9 or a fragment thereof the entire type A penton base gene of hemorrhagic enteritis virus (HEV) having the DNA sequence of SEQ ID NO:10 or a fragment thereof; and the entire envelope antigen gene of fowlpox virus (FPV) having the DNA sequence of SEQ ID NO:11 or a fragment thereof.

One preferred example of the DNA vaccine contains two DNA constructs, each containing a DNA molecule capable of expressing a gene or a fragment thereof which is from Marek's disease virus (MDV), infectious vursal disease virus (IBDV), Newcastle disease virus (NDV), or infectious bronchitis virus (IBV).

Another preferred example of the multiple DNA vaccine contains three or more DNA constructs, each containing a DNA molecule capable of expressing a gene or a fragment thereof which is from Marek's disease virus (MDV), infectious vursal disease virus (IBDV), Newcastle disease virus (NDV), or infectious bronchitis virus (IBV).

The present invention also provides a method for vaccinating fowl egg and a method for preparing the multiple DNA vaccine. The method for vaccinating fowl egg includes injecting into the fowl egg the multiple DNA vaccine as shown above. The method for preparing the multiple DNA vaccine includes ligating a DNA molecule to a plasmid or virus carrier to form a DNA construct; and then mixing two or more said DNA constructs to form the multiple DNA vaccine. The insertion of the DNA molecule into the vector can be achieved by conventional method, i.e., by ligation the DNA molecule with an enzyme such as T4 DNA ligase when both the genes and the desired vector have been cut with the same restriction enzyme(s) as complementary DNA termini are thereby produced. For pcDNA3, the preferred restriction enzymes are BamH1 and EcoR1.

In another embedment, there is provided a multivalent DNA vaccine for in ovo injection. The multivalent DNA vaccine comprises a DNA construct containing two or more DNA molecules linked together with a vector. Each of the DNA molecules expresses an antigenic protein of an avian virus, which is capable of inducing a protective immune response against that avian viral disease in fowl. The multivalent DNA vaccine is preferred to be injected into a fowl egg. Each of the DNA molecules of the multivalent DNA vaccine is a gene or a fragment thereof from Marek's disease virus (MDV), infectious vursal disease virus (IBDV), Newcastle disease virus (NDV), infectious bronchitis virus (IBV), infectious laryngotracheitis virus (ILTV), avian encephalomyelitis (AEV), avian leukosis virus (ALV), fowlpox virus (FPV), avian parainfluenza virus (APV), duck hepatitis virus (DHV), and hemorrhagic enteritis virus (HEV).

DETAILED DESCRIPTION OF THE INVENTION

Traditional avian vaccines comprise chemically inactivated virus vaccines or modified live-virus vaccines. Inactivated vaccines require additional immunizations which are not only expensive to produce but also laborious to administer. Further, some infectious virus particles may survive the inactivation process and may cause disease after administration to the animal.

In general, attenuated live virus vaccines are preferred over inactivated vaccines because they evoke an immune response often based on both humoral and cellular reactions. Such vaccines are normally based on serial passage of virulent strains in tissue culture. However, the attenuation process induces mutations of the viral genome, resulting in a population of virus particles heterogeneous with regard to virulence and immunizing properties. In addition, it is well known that the traditional attenuated live virus vaccines can revert to virulence resulting in disease outbreaks in inoculated animals and the possible spread of the pathogen to other animals.

Thus, it is advantageous for the industry to employ vaccines based on recombinant DNA technology. The resulting DNA vaccines only contain and express the necessary and relevant immunogenic material that is capable of eliciting a protective immune response against the pathogens and would not display above mentioned disadvantages of the live or inactivated vaccines.

For the purpose of preparing multiple DNA vaccines or multivalent recombinant DNA vaccines, the DNA sequence of the gene (also used interchangeably as "DNA molecule") need not contain the full length of DNA encoding the polypeptides. In most cases, a fragment of the gene which encodes an epitope region should be sufficient enough for immunization. The DNA sequence of an epitope region can be found by sequencing the corresponding part of other viral strains and comparing them. The major antigenic determinants are likely to be those showing the greatest heterology. Also, these regions are likely to lie accessibly in the conformational structure of the proteins. One or more such fragments of genes encoding the antigenic determinants can be prepared by chemical synthesis or by recombinant DNA technology. These fragments of genes, if desired, can be linked together or linked to other DNA molecules.

Also, the viral genes need not be in DNA. In fact, some of the frequently found avian viral diseases are caused by double- or single-stranded RNA viruses. For example, Marek's diesease virus is a double-stranded RNA virus, while infectious bursal disease virus (IBDV), Newcastle disease virus (NDV) and infectious bronchitis virus (IB) are single-stranded RNA viruses. The RNA viral sequences, however, can be reverse-transcribed into DNA using RT-Polymerase chain reaction (RT-PCR) technology and then incorporated into a vector by the conventional recombinant DNA technology In addition, because of the degeneracy of the genetic code it is possible to have numerous RNA and DNA sequences that encode a specified amino acid sequence. Thus, all RNA and DNA sequences which result in the expression of a polypeptide having the antibody binding characteristics are encompassed by this invention.

To construct a recombinant DNA vaccine, either univalent or multivalent, the DNA sequence of the viral gene can be ligated to other DNA molecules with which it is not associated or linked in nature. Optionally, the DNA sequence of a viral gene can be ligated to another DNA molecule, i.e., a vector, which contains portions of its DNA encoding fusion protein sequences such as β-galactosidase, resulting in a so-called recombinant nucleic acid molecule or DNA construct, which can be used for transformation of a suitable host. Such vector is preferably derived from, e.g., plasmids, or nucleic acid sequences present in bacteriophages, cosmids or viruses.

Specific vectors which can be used to clone nucleic acid sequences according to the invention are known in the art and include either a plasmid or a virus carrier. Examples of the plasmid include, but are not limited to, pBR322, pcDNA3, pVAX1, pSectag, pTracer, pDisplay, pUC system plasmids (e.g., pUC7, pUC8, pUC18), pGEM system plasmids, Bluescript plasmids or any other plasmids where CMV promoter, SV40 promoter, RSV promoter, or β-actin promoter is included. The preferred plasmid is pcDNA3. Examples of the virus carrier include, but are not limited to, bacteriophages (e.g., λ and the M13-derived phages), SV40, adenovirus, polyoma, baculoviruses, herpes viruses (HVT) or pox viruses (e.g., fowl pox virus).

The methods to be used for the construction of a recombinant nucleic acid molecule are known to those of ordinary skill in the art. For example, the insertion of the nucleic acid sequence into a cloning vector can easily be achieved by ligation with an enzyme such as T4 DNA ligase when both the genes and the desired cloning vehicle have been cut with the same restriction enzyme(s) so that complementary DNA termini are thereby produced.

Alternatively, it may be necessary to modify the restriction sites so as to produce blunt ends either by digesting the single-stranded DNA or by filling in the recessive termini with an appropriate DNA polymerase. Subsequently, blunt end ligation with an enzyme such as T4 DNA ligase may be carried out. If desired, any restriction site may be produced by ligating linkers onto the DNA termini. Such linkers may comprise specific oligonucleotide sequences that encode restriction site sequences. The restriction enzyme cleaved vector and nucleic acid sequence may also be modified by homopolymeric tailing.

The present invention provides two kinds of DNA vaccines. The first kind is a multiple DNA vaccine, which includes two or more of univalent DNA vaccines, each containing a DNA sequence encoding at least one polypeptide affording protection against one viral disease such as Marek's dosease voris (MDV), infectious bursal disease virus (IBDV), Newcastle disease virus (NDV), infectious bronchitis virus (IBV), infectious laryngotracheitis virus (ILTV), avian encephalomyelitis (AEV), Fowlpox virus (FPV), avian influenza virus (AIV), avian leukosis virus (ALV), duck hepatitis virus B genome, and hemorrhagic enteritis virus (HEV), inserted into a commercially available plasmid.

The second kind is a multivalent recombinant DNA vaccine, which contains two or more genes or gene fragments from different viruses. These genes or gene fragments are carried by a useful vector, which can be either a plasmid or a virus carrier. The multivalent recombinant DNA vaccine encodes two or more antigenic polypeptides which afford protection against at least two viral diseases including, but not limited to, MD, IBD, ND or IB. The viral genes or gene fragments are operatively attached to the vector in reading frame so that they can be expressed in a host. The different structural DNA sequences carried by the vector may be separated by termination and start sequences so that the proteins can be expressed separately or they may be part of a single reading frame and therefore be produced as a fusion protein by methods known in the art.

The preferred DNA sequences include, but are not limited to, the entire of gB gene of Merk's Disease virus (MDV) having the DNA sequence of SEQ ID NO:1 or a fragment thereof; the entire VP2 gene of infectious bursal disease virus (IBDV) having the DNA sequence of SEQ ID NO:2 or a fragment thereof; the entire HN gene of Newcastle disease virus (NDV) having the DNA sequence of SEQ ID NO:3 or a fragment thereof; the entire S1 gene of infectious bronchitis virus (IBV) having the DNA sequence of SEQ ID NO:4 or a fragment thereof.

The DNA sequence encoding the gB polypeptide of MDV has the nucleic acid sequence as SEQ ID NO:1. The DNA sequence contains 3650 bp of linear DNA.

The DNA sequence encoding the VP2 polypeptide of IBDV has the nucleic acid sequence as SEQ ID NO:2. The DNA sequence contains 3004 bp of linear DNA molecule which is reversely transcribed from IBDV's RNA template.

The DNA sequence of the entire genome of NDV contains 15186 bps of DNA, wherein (1) base No. 56 to 1792 encodes NP polypeptide, which is nucleocapsid protein; (2) base No. 1804–3244 encodes P polypeptide, which is a phosphoprotein; (3) base No. 3256–4487 encodes M polypeptide, which is a matrix protein; (4) base No. 4498–6279 encodes F polypeptide, which is a fusion protein; (5) base 6321–8319 encodes HN polypeptide, which is a hemagglutinin-neuraminidase; (6) base No. 8370–15073 encodes L polypeptide, which is a large polymerase protein. The NDV genome has the DNA sequence as SEQ ID NO:3.

The DNA sequence of the Si polypeptide contains 1611 bp of linear DNA sequence as shown in SEQ ID NO:4, which is reversely transcribed from IBV's RNA templates.

The following experimental designs are illustrative, but not limiting the scope of the present invention. Reasonable variations, such as those occur to reasonable artisan, can be made herein without departing from the scope of the present invention.

I. Materials and Methods

(A) Virus and Vaccines

Avian infectious bronchitis virus (IBV), infectious bursal disease (IBD) and Newcastle disease (ND) vaccines were purchased from Intervet Inc.

(B) Viral RNA Isolation and RT-PCR

Two hundred microliter recovered attenuated vaccines (Intervet Inc.) were resolved in iced cold GTC buffer (4 M guanidium isothiocyanate, 25 mM sodium citrate, pH 7.0, 0.5% Sarkosyl, 0.1 M-mercaptoethanol) and sodium acetate (pH 4). An equal volume of phenol-chloroform (1:1) was added and placed on ice for 15 minutes after vortexing. The aqueous phase was collected after centrifuge and the RNA was precipitated with an equal volume of isopropanol. RNA was pelleted by centrifugation at 12000 rpm for 20 min at 4° C. and then suspended in diethylpyrocarbonate (DEPC) treated deionized distill water and stored at −70° C.

(C) Oligonucleotides

Oligonucleotide primers for RT-PCR amplification were purchased from Promega, and were designed according to the genome of the Avian infectious bronchitis virus (Beaudette CK strain), Newcastle disease virus (Lasota strain) and Infectious bursa disease virus respectively. The sequences of the primers used for PCR were:

```
IBS1F'
                                           (SEQ ID NO:12)
5' CGGGATCCGCCGCCGCCATGTTGGTAACACCTCTT 3';

IBS1R'
                                           (SEQ ID NO:13)
5' CGGAATTCTTAACGTCTAAAACGACGTGT 3';

NDF F'
                                           (SEQ ID NO:14)
5' CGGGATCCGCCGCCGCCATGGGCTCCAGACCTTCTACC 3';

NDF R'
                                           (SEQ ID NO:15)
5' CCGCTCGAGTTACATTTTTGTAGTGGCTCTCATT 3';

NDHN F'
                                           (SEQ ID NO:16)
5' CGGGATCCGCCGCCGCCATGGACCGCGCCGTTAGGCAAG 3';

NDHN R'
                                           (SEQ ID NO:17)
5' GCTCTAGATTACTCAACTAGCCAGACCTG 3';

IBDVP2F'
                                           (SEQ ID NO:18)
5' CGGGATCCGCCGCCGCCATGACAAACCTGCAAGAT 3';

IBDVP2R'
                                           (SEQ ID NO:19)
5' CGGAATTCTTACCTTATGGCCCGGATTAT 3'.
```

(D) Reverse Transcription Polymerase Reaction (RT-PCR)

Reverse transcription of IBV, NDV and IBDV RNA were carried out at 42° C. for 30 min in 2.5× Taq buffer (200 mM NaCl, 15 mM Tris-HCl, pH7.4, 15 mM MgCl$_2$, 15 mM β-mercaptoethanol, and 0.25 mM each of dATP, dCTP, dGTP, and dTTP). In addition to the Taq buffer, the reaction mixture (40 μl) also contained viral RNA, 2.4 U of avian myeloblastosis virus (AMV) reverse transcriptase (Promega), 16 U of RNasin (Promega), and 0.01 nmol reverse primer (IBDVP2R, NDF F, NDHN F or IBS1R). The final volume of the reaction mixture was 40 μl. After reverse transcription, the following reagents were added to the reverse transcription mixture: 0.02 nmol of each nucleotide triphosphate (dATP, dCTP, dGTP, dTTP), 0.01 nmol of forward primer (IBDVP2F, NDF R, NDHN R or IBS1F) and 1.5 U of Taq DNA polymerase (Strategene). Water was then added to a final volume of 100 μl. The reaction was carried out for 32 cycles in a Thermal Cycler (Perkin Elmer-Cetus). Each PCR cycle consisted of 1 min of denaturation at 94° C., 1 min of annealing at 57° C., and 2 min of DNA chain elongation at 72° C.

(E) Preparation of DNA Constructs

The plasmids pCMV-VP2, pCMV-S1, pCMV-NDF and pCMV-NDHN were constructed with the VP2, S1, NDF and NDHN genes from IBD vaccine, IBV vaccine and NDV vaccine respectively, placed downstream of the commercial plasmid pcDNA3. (Invitrogen, U.S.A.). All of the genes were inserted into the pcDNA3 vector using restriction enzymes BamH1, EcoR1, XbaI and XhoI (underlined characters in the sequence of the primers). Sequences of the all genes in the pcDNA3 vector were verified by sequencing in both directions.

(F) Preparation of DNA and DNA Delivery

The quantity of plasmid DNA that had been purified by affinity chromatography (Qiagen. Inc.) was determined by spectrophotometric measurements at 260 and 280 nm. The DNA in aliquots to 100 μg was suspended in 100 μl of PBS (0.14M NaCl, 10 mM sodium phosphate, pH 7.4). For DNA delivery, 1 cc syringe with a 20 gauge 1 and ½ inch needle were used. For the in-ovo groups, the embryos (18-day-old fertilized and developing eggs from the setting trays) were injected with 0.1 milliliters of DNA vaccine (100 μg) into the large end of each egg through the air cell with a needle. The eggs were then transferred into the hatchery where they remained until they hatched at about 21 days of age. For the IM (Intramuscular), all of the vaccines (⅕ dose of live vaccines) were injected into the chicken's thoracic muscle at 10 days post hatchery.

II. Experimental Design

Specific Pathogen Free (SPF) fertilized eggs (n=60) were randomized into 12 groups. All groups (five eggs each group), all eggs were given 100 μl in volume each. 100 μg pCMV-NDF+100 μg pCMV-NDHN mixture was injected in each egg of group A, 100 μg pCMV-S1 was injected in each egg of group B, 100 μg pCMV-VP2 was injected in each egg of group C, 100 μg pCMV-NDF+100 μg pCMV-NDHN+ 100 μg pCMV-S1(ND+IB) was injected in each egg of group D, 100 μg pCMV-NDF+100 μg pCMV-NDHN+100 μg pCMV-VP2 (ND+IBD) was injected in each egg of group E, 100 μg pCMV-VP2+100 μg pCMV-VP2 mixture (IB+IBD) was injected in each egg of group F, 100 μg pCMV-NDF+ 100 μg pCMV-NDHN+100 μg pCMV-S1+100 μg pCMV-VP2 mixture (ND+IB+IBD) was injected in each egg of group G, one dose of commercialized in-ovo IBD vaccine (Embrex, Inc) was injected in each egg of group H as positive control, 100 ul PBS was injected in each egg of group I, J, K and L. All chickens in this experiment were given 100 μl in volume (⅕ dose of live vaccines), injected into the chicken's thoracic muscle each at 10 days post hatchery. Chickens in group A and I were injected with NDV vaccine, group B and J were injected with IBV vaccine, group C and K were injected with IBDV vaccine, group D were injected with the mixture of NDV+IB vaccines, group E were injected with the mixture of NDV+IBD vaccines, group F were injected with the mixture of IB+IBD vaccines and group G and L were injected with the mixture of NDV, IB and IBD vaccines.

III. Serology Detection

All of the serum samples were collected at 10 days (injected with low dose live vaccines at the same time), 17 days, 24 days and 31 days post hatchery. The antibody titers were detected by ELISA using IB, IBD and NDV antibody test kits which purchased from IDEXX Laboratories, Inc. All of the samples were detected duplicated. Dilute test samples five hundred fold (1:500) with sample diluents prior to being assayed. The test procedure was applied according to the kit's manual. For the assay to be valid, measure and record absorbance values at 650 nm, A (650). The relative level of antibody in the unknown was determined by calculating the sample to positive (S/P) ratio. Endpoint titers were calculated using the formula: $\mathrm{Log}_{10}\mathrm{Titer} = 1.09 (\mathrm{Log}_{10}\mathrm{S/P}) + 3.36$ Results As shown in Table 1, the results demonstrated that, for the detection of anti-IBD antibodies, the IBDV recombinant antigens VP2 could be expressed and played the role of primary stimulation. The titers increased rapidly after a low dose vaccine booster. The titers of group C, E, F and G at 17 days post hatchery (i.e. 7 days post IM injection) were significantly higher than those of group K and L. Most importantly, the expression of IBDV antigen was not interfered by other monovalent DNA vaccines (NDV and IBV). The same results were also applied to IB and NDV DNA vaccines. The titers of group B, D, F and G were higher than those of group J and L at 17 days post hatchery (Table 2) and the titers of group A, D, E and G were higher than those of group I and L at 17 days post hatchery (Table 3). The only unpredicted result was the anti-NDV titer could not be highly induced by the triple valent DNA vaccine (Table 3, group G), but anti-IBD and anti-IB did (Tables 1 and 2, group G).

TABLE 2-continued

Serum Samples Detected by IDEXX IB Antibody test kit (Ab Titers Correspond to the Average Titers ±SD
Immunization and Sample Collection Schedule (days)

| Animal Group | 10 Days PH* | 17 Days PH | 24 Days PH | 31 Days PH |
|---|---|---|---|---|
| G(IBD+ IB + ND) | — | 499 ± 81 | 688 ± 78 | 2551 ± 531 |
| J(PBS/IB) | — | — | 485 ± 76 | 1662 ± 441 |
| L(PBS/IBD + IB + ND) | — | — | 819 ± 202 | 1332 ± 488 |

*PH: post hatchery
**—: average titers less than 396 (be considered negative by IDEXX kit)

TABLE 3

Serum Samples Detected by IDEXX ND Antibody Test Kit (Ab Titers Correspond to the Average Titers ±SD).
Immunization and Sample Collection Schedule (days)

| Animal Group | 10 Days PH* | 17 Days PH | 24 Days PH | 31 Days PH |
|---|---|---|---|---|
| A(ND) | — | 466 ± 101 | 2394 ± 456 | 8103 ± 2198 |
| D(ND + IB) | — | 706 ± 140 | 1778 ± 378 | 6811 ± 2206 |
| E(ND + IBD) | — | 517 ± 104 | 3021 ± 411 | 5991 ± 1695 |
| G(IBD + IB + ND) | — | — | — | 783 ± 201 |
| I(PBS/ND) | — | — | 1853 ± 324 | 3912 ± 304 |
| L(PBS/IBD + IB + ND) | — | — | 4027 ± 662 | 5807 ± 1996 |

*PH: post hatchery
**—: average titers less than 396 (be considered negative by IDEXX kit)

TABLE 1

Serum Samples Detected by IDEXX IBD Antibody Test Kit (Ab Titers Correspond to the Average Titers ±SD)
Immunization and Sample Collection Schedule (days)

| Animal Group | 10 Days PH* | 17 Days PH | 24 Days PH | 31 Days PH |
|---|---|---|---|---|
| C(IBD) | —** | 4535 ± 1267 | 16623 ± 3105 | 21254 ± 3852 |
| E(IBD + ND) | — | 1685 ± 655 | 17339 ± 2185 | 19041 ± 2967 |
| F(IBD + IB) | — | 8252 ± 2205 | 10057 ± 1295 | 17561 ± 2006 |
| G(IBD + IB + ND) | — | 9111 ± 1701 | 13127 ± 1763 | 16694 ± 2134 |
| H(IBD positive) | 6553 ± 851 | 13025 ± 2131 | 18015 ± 1592 | 18853 ± 2614 |
| K(PBS/IBD) | — | — | 1853 ± 302 | 17002 ± 2965 |
| L(PBS/IBD + IB + ND) | — | — | 6923 ± 1168 | 18063 ± 2531 |

*PH: post hatchery
**—: average titers less than 396 (be considered negative by IDEXX kit)

TABLE 2

Serum Samples Detected by IDEXX IB Antibody test kit (Ab Titers Correspond to the Average Titers ±SD
Immunization and Sample Collection Schedule (days)

| Animal Group | 10 Days PH* | 17 Days PH | 24 Days PH | 31 Days PH |
|---|---|---|---|---|
| B(IB) | —** | 441 ± 117 | 2426 ± 264 | 3214 ± 877 |
| D(IB + ND) | — | 586 ± 182 | 805 ± 221 | 1988 ± 501 |
| F(IB + IBD) | — | 509 ± 89 | 685 ± 186 | 1192 ± 237 |

I claim:

1. A method for vaccinating a fowl egg comprising:
injecting into an amniotic fluid of said fowl egg a multiple DNA vaccine, the multiple DNA vaccine comprising:
two or more DNA constructs, each of said DNA constructs containing a DNA molecule and a vector;
wherein said DNA molecule comprises a gene or a fragment thereof encoding an antigenic peptide of an avian virus causing an avian viral disease in fowl;
wherein said antigenic peptide of said avian virus is capable of inducing a protective immune response against said avian viral disease in said fowl;
wherein said vector is a plasmid or a viral carrier;
wherein said viral carrier is selected from the group consisting of a bacteriophage, an SV40, an adenovirus, a polyoma virus, a vaccinia virus, a baculovirus, and a pox virus; and
wherein said avian virus is selected from the group consisting of Marek's disease virus (MDV), infectious bursal disease virus (IBDV), Newcastle disease virus (NDV), infectious bronchitis virus (IBV), infectious laryngotracheitis virus (ILTV), avian leucosis virus (ALV), duck hepatitis virus (DHV), and hemorrhagic enteritis virus (HEV).

2. A method for vaccinating a fowl egg comprising:
injecting into an amniotic fluid of said fowl egg a multivalent DNA vaccine, said multivalent DNA vaccine comprising:
a DNA construct containing two or more DNA molecules ligated to a vector, wherein each of said DNA molecules contains a gene or a fragment thereof encoding an antigenic peptide of an avian virus causing an avian viral disease in fowl;
wherein said antigenic peptide of said avian virus is capable of inducing a protective immune response against said avian viral disease in said fowl;
wherein said vector is a plasmid or a viral carrier;
wherein said viral carrier is selected from the group consisting of a bacteriophage, an SV40, an adenovirus, a polyoma virus, a vaccinia virus, and a baculovirus; and
wherein said avian virus is selected from the group consisting of Marek's disease virus (MDV), infectious bursal disease virus (IBDV), Newcastle disease virus (NDV), infectious bronchitis virus (IBV), infectious laryngotracheitis virus (ILTV), avian leucosis virus (ALV), duck hepatitis virus (DHV), and hemorrhagic enteritis virus (HEV).

3. A method for delivering a multiple DNA vaccine to a fowl, the method comprising:
injecting said multiple DNA vaccine into an amniotic fluid of an egg of said fowl, the multiple DNA vaccine comprising:
two or more DNA constructs, each of said DNA constructs containing a DNA molecule and a vector;
wherein said DNA molecule comprises a gene or a fragment thereof encoding an antigenic peptide of an avian virus causing an avian viral disease in fowl;
wherein said antigenic peptide of said avian virus is capable of inducing a protective immune response against said avian viral disease in said fowl;
wherein said vector is a plasmid or a viral carrier;
wherein said viral carrier is selected from the group consisting of a bacteriophage, an SAV40, an adenovirus, a polyoma virus, a vaccinia virus, a baculovirus, and a pox virus; and
wherein said avian virus is selected from the group consisting of Marek's disease virus (MDV), infectious bursal disease virus (IBDV), Newcastle disease virus (NDV), infectious bronchitis virus (IBV), infectious laryngotracheitis virus (ILTV), avian leucosis virus (ALV), duck hepatitis virus (DHV), and hemorrhagic enteritis virus (HEV).

4. The method according to claim 3, wherein said DNA vaccine is injected into a large end of said egg through an air cell with a needle.

5. The method according to claim 4, wherein said needle is a 20 gauge 1 and ½ inch needle.

6. A method for delivering a multivalent DNA vaccine to a fowl, the method comprising:
injecting said multivalent DNA vaccine into an amniotic fluid of an egg of said fowl, said multivalent DNA vaccine comprising:
a DNA construct containing two or more DNA molecules ligated to a vector, wherein each of said DNA molecules contains a gene or a fragment thereof encoding an antigenic peptide of an avian virus causing an avian viral disease in fowl;
wherein said antigenic peptide of said avian virus is capable of inducing a protective immune response against said avian viral disease in said fowl;

wherein said vector is a plasmid or a viral carrier;
wherein said viral carrier is one selected from the group consisting of a bacteriophage, an SV40, an adenovirus, a polyoma virus, a vaccinia virus, and a baculovirus; and
wherein said avian virus is one selected from the group consisting of Marek's disease virus (MDV), infectious bursal disease virus (IBDV), Newcastle disease virus (NDV), infectious bronchitis virus (IBV), infectious laryngotracheitis virus (ILTV), avian leucosis virus (ALV), duck hepatitis virus (DHV), and hemorrhagic enteritis virus (HEV).

7. The method according to claim 6, wherein said DNA vaccine is injected into a large end of said egg through an air cell with a needle.

8. The method according to claim 7, wherein said needle is a 20 gauge 1 and ½ inch needle.

9. A method for vaccinating a fowl egg comprising:
injecting into an amniotic fluid of said fowl egg a multivalent DNA vaccine, said multivalent DNA vaccine comprising:
a DNA construct containing two or more DNA molecules ligated to a vector, wherein each of said DNA molecules contains a gene or a fragment thereof encoding an antigenic peptide of an avian virus causing an avian viral disease in fowl;
wherein said antigenic peptide of said avian virus is capable of inducing a protective immune response against said avian viral disease in said fowl;
wherein said vector is a plasmid; and
wherein said avian virus is one selected from the group consisting of Marek's disease virus (MDV), infectious bursal disease virus (IBDV), Newcastle disease virus (NDV), infectious bronchitis virus (IBV), infectious laryngotracheitis virus (ILTV), avian leucosis virus (ALV), duck hepatitis virus (DHV), and hemorrhagic enteritis virus (HEV).

10. A method for delivering a multivalent DNA vaccine to a fowl, the method comprising:
injecting said multivalent DNA vaccine into an amniotic fluid of an egg of said fowl, said multivalent DNA vaccine comprising:
a DNA construct containing two or more DNA molecules ligated to a vector, wherein each of said DNA molecules contains a gene or a fragment thereof encoding an antigenic peptide of an avian virus causing an avian viral disease in fowl;
wherein said antigenic peptide of said avian virus is capable of inducing a protective immune response against said avian viral disease in said fowl;
wherein said vector is a plasmid; and
wherein said avian virus is one selected from the group consisting of Marek's disease virus (MDV), infectious bursal disease virus (IBDV), Newcastle disease virus (NDV), infectious bronchitis virus (IBV), infectious laryngotracheitis virus (ILTV), avian leucosis virus (ALV), duck hepatitis virus (DHV), and hemorrhagic enteritis virus (HEV).

11. The method according to claim 1, wherein said DNA vaccine is injected into a large end of said egg through an air cell with a needle.

12. The method according to claim 1, wherein the vector is a plasmid.

13. The method according to claim 1, wherein the fowl egg is a chicken egg.

14. The method according to claim 1, wherein the fowl egg is a turkey egg.

15. The method according to claim 1, wherein the egg is fertilized for about 18 days.

16. The method according to claim 2, wherein said DNA vaccine is injected into a large end of said egg through an air cell with a needle.

17. The method according to claim 2, wherein the fowl egg is a chicken egg.

18. The method according to claim 2, wherein the fowl egg is a turkey egg.

19. The method according to claim 2, wherein the egg is fertilized for about 18 days.

20. The method according to claim 3, wherein the vector is a plasmid.

21. The method according to claim 3, wherein the fowl is a chicken.

22. The method according to claim 3, wherein the fowl is a turkey.

23. The method according to claim 3, wherein the egg is fertilized for about 18 days.

24. The method according to claim 6, wherein the fowl is a chicken.

25. The method according to claim 6, wherein the fowl egg is a turkey egg.

26. The method according to claim 6, wherein the egg is fertilized for about 18 days.

* * * * *

SEQUENCE LISTING

<160> NUMBER OF SEQ ID NOS: 19

<210> SEQ ID NO 1
<211> LENGTH: 3650
<212> TYPE: DNA
<213> ORGANISM: Marek's disease virus

<400> SEQUENCE: 1

```
tcgagctcgc cggggatgtt tagtcacgat agacatcggt tcgcccagcc gtcgaataca     60
gcattatatt ttagtgttga aaatgtaggg ctgcttcctc acttaaagga ggaaatggct    120
cgattcatgt ttcatagcag tagaaaaaca gattggaccg tcagtaagtt tagagggttt    180
tatgacttta gcactataga taatgtaact gcggcccatc gcatggcttg gaaatatatc    240
aaagaactga tttttgcaac agctttattt tcttctgtat ttaaatgtgg cgaattgcac    300
atctgtcgtg ccgacagttt gcagatcaac agcaatggag actatgtatg gaaaaatgga    360
atatatataa catatgaaac cgaatatcca cttataatga ttctggggtc agaatcaagc    420
acttcagaaa cgcaaaatat gactgcaatt attgatacag atgttttttc gttgctttat    480
tctattttgc agtatatggc cccgttacg gcagatcagg tgcgagtaga acagattacc     540
aacagccacg cccccatctg acccgtccaa tattcttgtg tccctgcatt ttatctcaca    600
caatttatga acagcatcat taagatcatc tcactatgca ctattttagg cggaattgca    660
tttttttcct tatagttatt ctatatggta cgaactcatc tccgagtacc caaaatgtga    720
catcaagaga agttgtttcg agcgtccagt tgtctgagga agagtctacg ttttatcttt    780
gtcccccacc agtgggttca accgtgatcc gtctagaacc gccgcgaaaa tgtcccgaac    840
ctagaaaagc caccgagtgg ggtgaaggaa tcgcgatatt atttaaagag aatatcagtc    900
catataaatt taaagtgacg ctttattata aaaatatcat tcagacgacg acatggacgg    960
ggacgacata tagacagatc actaatcgat atacagatag gacgcccgtt tccattgaag   1020
agatcacgga tctaatcgac ggcaaaggaa gatgctcatc taaagcaaga taccttagaa   1080
acaatgtata tgttgaagcg tttgacaggg atgcgggaga aaaacaagta cttctaaaac   1140
catcaaaatt caacacgccc gaatctaggg catggcacac gactaatgag acgtataccg   1200
tgtggggatc accatggata tatcgaacgg gaacctccgt caattgtata gtagaggaaa   1260
tggatgcccg ctctgtgttt ccgtattcat attttgcaat ggccaatggc gacatcgcga   1320
acatatctcc attttatggt ctatccccac cagaggctgc cgcagaaccc atgggatatc   1380
cccaggataa tttcaaacaa ctagatagct atttttcaat ggatttggac aagcgtcgaa   1440
aagcaagcct tccagtcaag cgtaactttc tcatcacatc acacttcaca gttgggtggg   1500
actgggctcc aaaaactact cgtgtatgtt caatgactaa gtggaaagag gtgactgaaa   1560
tgttgcgtgc aacagttaat gggagataca gatttatggc ccgtgaactt tcggcaacgt   1620
ttatcagtaa tacgactgag tttgatccaa atcgcatcat attaggacaa tgtattaaac   1680
gcgaggcaga agcagcaatc gagcagatat ttaggacaaa atataatgac agtcacgtca   1740
aggttggaca tgtacaatat ttcttggctc tcgggggatt tattgtagca tatcagcctg   1800
ttctatccaa atccctggct catatgtacc tcagagaatt gatgagagac aacaggaccg   1860
atgagatgct cgacctggta aacaataagc atgcaattta taagaaaaat gctacctcat   1920
tgtcacgatt gcggcgagat attcgaaatg caccaaatag aaaaataaca ttagacgaca   1980
ccacagctat taaatcgaca tcgtctgttc aattcgccat gctccaattt ctttatgatc   2040
```

-continued

```
atatacaaac ccatattaat gatatgttta gtaggattgc cacagcttgg tgcgaattgc    2100
agaatagaga acttgtttta tggcacgaag ggataaagat taatcctagc gctacagcga    2160
gtgcaacatt aggaaggaga gtggctgcaa agatgttggg ggatgtcgct gctgtatcga    2220
gctgcactgc tatagatgcg gaatccgtca ctttgcaaaa ttctatgcga gttatcacat    2280
ccactaatac atgttatagc cgaccattgg ttctattttc atatggagaa accaaggaa     2340 acatacaggg acaactcggt gaaaacaacg agttgcttcc aacgctagag ctgtagagc     2400 catgctcggc taatcatcgt agatattttc tgtttggatc cggttatgct ttatttgaaa    2460
actataattt tgttaagatg gtagacgctg ccgatataca gattgctagc acatttgtcg    2520
agcttaatct aaccctgcta aagatcgggg aaattttgcc tttatccgtt tacacaaaag    2580
aagagttgcg tgatgttggt gtattggatt atgcagaagt agctcgccgc aatcaactac    2640
atgaacttaa attttatgac ataaacaaag taatagaagt ggatacaaat tacgcgttta    2700
tgaacggttt ggccgaattg tttaacggta tgggtcaggt agggcaagct ataggcaaag    2760
ttgtagtagg ggctgccggt gcaatcgtat ctaccatatc tggtgtctct gctttcatgt    2820
caatcccttt ggggctttcg gcaatcggtt taatcattat agcaggactc gtggctgcat    2880
ttttagcata tcgttatgta aacaagctta aaagcaatcc aatgaaagcc ctttatccta    2940
tgacaacaga agtgcttaag gcacaggcaa cgcgtgagtt gcatggcgag gaatcagatg    3000
atttggaacg aacatctatt gatgaaagaa aattagaaga agctagagaa atgataaaat    3060
atatggcgtt agtctccgcg gaagaacgcc acgagaaaaa actgcggaga aagaggcgag    3120
gcactaccgc cgttctatcg gaccacctgg caaaaatgag gattaaaaat agtaacccta    3180
aatatgataa gttacctact acatattcag actcagaaga tgatgctgtg taagtgggca    3240
ctattatatt tgaactgaat aaaacgcata gagcatgata tggtttactc atttattgcg    3300
agatataaag catattcaat acgatatatt gcgaacgtga tgctaaaaac atagctccct    3360
gtattattga tgcgccatca tttgattaat aaatacatcg acgccggcat cactggtgcg    3420
gtgtatacca gctacggcgc tagcattcat ggtatcccgt gattgctcga tgctttcctt    3480
ctgaattccg tcggaacgct cctgagagat ggtcgcagtt attggtacat ttcgaccagc    3540
ctccggatct gaaactggca caggaatgca ccgtggaatt ggtagaagtt tttccttccg    3600
tggaaggcat agggcgttcg actcccatgg gccatgaaac tgtgggatgt              3650
```

<210> SEQ ID NO 2
<211> LENGTH: 3004
<212> TYPE: DNA
<213> ORGANISM: infectious bursal disease virus (IBDV)

<400> SEQUENCE: 2

```
tgatgccaac aaccggaccg gcgtccattc cggacgacac cctggagaag cacactctca     60
ggtcagagac ctcgacctac aatttgactg tggggggacac agggtcaggg ctaattgtct    120 tttccctgg attccctggc tcaattgtgg gtgctcacta cacactgcag agcaatggga    180
actacaagtt cgatcagatg ctcctgactg cccagaacct accggccagt tacaactact    240
gcaggctagt gagtcggagt ctcacagtga ggtcaagcac acttcctggt ggcgtttatg    300
cactaaacgg caccataaac gccgtgacct tccaaggaag cctgagtgaa ctgacagatg    360
ttagctacaa tgggttgatg tctgcaacag ccaacatcaa cgacaaaatt gggaacgtcc    420
tagtagggga agggggtcacc gtcctcagct tacccacatc atatgatctt gggtatgtga    480
```

-continued

```
ggcttggtga ccccattccc gcaatagggc ttgacccaaa aatggtagcc acatgtgaca      540
gcagtgacag gcccagagtc tacaccataa ctgcagccga tgattaccaa ttctcatcac      600
agtaccaacc aggtggggta acaatcacac tgttctcagc caacattgat gccatcacaa      660
gcctcagcgt tgggggagag ctcgtgtttc gaacaagcgt ccacggcctt gtactgggcg      720
ccaccatcta cctcataggc tttgatggga acaggtaat caccagggct gtggccgcaa       780
acactgggct gacgaccggc accgacaacc ttatgccatt caatcttgtg attccaacaa      840
acgagataac ccagccaatc acatccatca aactggagat agtgacctcc aaaagtggtg      900
gtcaggcagg ggatcagatg ttatggtcgg caagagggag cctagcagtg acgatccatg      960
gtggcaacta tccaggggcc ctccgtcccg tcacgctagt ggcctacgaa agagtggcaa     1020
caggatccgt cgttacggtc gctggggtga gcaacttcga gctgatccca aatcctgaac     1080
tagcaaagaa cctggttaca gaatacggcc gatttgaccc aggagccatg aactacacaa     1140
aattgatact gagtgagagg gaccgtcttg gcatcaagac cgtctggcca acaagggagt     1200
acactgactt tcgtgaatac ttcatggagg tggccgacct caactctccc ctgaagattg     1260
caggagcatt cggcttcaaa gacataatcc gggcctaag gaggatagct gtgccggtgg      1320
tctccacatt gttcccacct gccgctcccc tagcccatgc aattggggaa ggtgtagact     1380
acctgctggg cgatgaggca caggctgctt caggaactgc tcgagccgcg tcaggaaaag     1440
caagagctgc ctcaggccgc ataaggcagc tgactctcgc cgccgacaag gggtacgagg     1500
tagtcgcgaa tctattccag gtgccccaga atcccgtagt cgacgggatt cttgcttcac     1560
ctggggtact ccgcggtgca cacaacctcg actgcgtgtt aagagagggt gccacgctat     1620
tccctgtggt tattacgaca gtggaagacg ccatgacacc caaagcattg aacagcaaaa     1680
tgtttgctgt cattgaaggc gtgcgagaag acctccaacc tccatctcaa agaggatcct     1740
tcatacgaac tctctctgga cacagagtct atggatatgc tccagatggg gtacttccac     1800
tggagactgg gagagactac accgttgtcc aatagatga tgtctgggac gacagcatta     1860
tgctgtccaa agatcccata cctcctattg tgggaaacag tggaaatcta gccatagctt     1920
acatggatgt gtttcgaccc aaagtcccaa tccatgtggc tatgacggga gccctcaatg     1980
cttgtggcga gattgagaaa gtaagcttta gaagcaccaa gctcgccact gcacaccgac     2040
ttggccttaa gttggctggt cccggagcat tcgatgtaaa caccgggccc aactgggcaa     2100
cgttcatcaa acgtttccct cacaatccac gcgactggga caggctcccc tacctcaacc     2160 taccataccct tccacccaat gcaggacgcc agtaccacct tgccatggct gcatcagagt     2220
tcaaagagac ccccgaactc gagagtgccg tcagagcaat ggaagcagca gccaacgtgg     2280
acccactatt ccaatctgca ctcagtgtgt tcatgtggct ggaagagaat gggattgtga     2340
ctgacatggc caacttcgca ctcagcgacc cgaacgccca tcggatgcga aattttcttg     2400
caaacgcacc acaagcaggc agcaagtcgc aaagggccaa gtacgggaca gcaggctacg     2460
gagtggaggc tcgggccccc acaccagagg aagcacagag ggaaaaagac acacggatct     2520
caaagaagat ggagaccatg ggcatctact ttgcaacacc agaatgggta gcactcaatg     2580
ggcaccgagg gccaagcccc ggccagctaa agtactggca gaacacacga gaaataccgg     2640
acccaaacga ggactatcta gactacgtgc atgcagagaa gagccggttg gcatcagaag     2700
aacaaatcct aagggcagct acgtcgatct acggggctcc aggacaggca gagccacccc     2760
aagctttcat agacgaagtt gccaaagtct atgaaatcaa ccatggacgt ggcccaaacc     2820
aagaacagat gaaagatctg ctcttgactg cgatggagat gaagcatcgc aatcccaggc     2880
```

```
gggctctacc aaagcccaag ccaaaaccca atgctccaac acagagaccc cctggtcggc    2940
tgggccgctg atcaggacc gtctctgatg aggaccttga gtgaggctcc tggaagtctc     3000
ccga                                                                  3004
```

<210> SEQ ID NO 3
<211> LENGTH: 15186
<212> TYPE: DNA
<213> ORGANISM: Newcastle disease virus (NDV)

<400> SEQUENCE: 3

```
accaaacaga gaatccgtga gttacgataa aaggcgaagg agcaattgaa gtcgcacggg    60
tagaaggtgt gaatctcgag tgcgagcccg aagcacaaac tcgagaaagc cttctgccaa    120
catgtcttcc gtatttgatg agtacgaaca gctcctcgcg gctcagactc gccccaatgg    180
agctcatgga gggggagaaa aagggagtac cttaaaagta gacgtcccgg tattcactct    240
taacagtgat gacccagaag atagatggag ctttgtggta ttctgcctcc ggattgctgt    300
tagcgaagat gccaacaaac cactcaggca aggtgctctc atatctcttt tatgctccca    360
ctcacaggta atgaggaacc atgttgccat tgcagggaaa cagaatgaag ccacattggc    420
cgtgcttgag attgatggct ttgccaacga cacgccccag ttcaacaata ggagtggagt    480
gtctgaagag agagcacaga gatttgcgat gatagcagga tctctccctc gggcatgcag    540
caacggaacc ccgttcgtca cagccggggc agaagatgat gcaccagaag acatcaccga    600
taccctggag aggatcctct ctatccaggc tcaagtatgg gtcacagtag caaaagccat    660
gactgcgtat gagactgcag atgagtcgga acaaggcga atcataagt atatgcagca    720
aggcagggtc caaagaaat acatcctcta ccccgtatgc aggagcacaa tccaactcac    780
gatcagacag tctcttgcag tccgcatctt tttggttagc gagctcaaga gaggccgcaa    840
cacggcaggt ggtacctcta cttattataa cctggtaggg gacgtagact catacatcag    900
gaataccggg cttactgcat tcttcttgac actcaagtac ggaatcaaca ccaagacatc    960
agcccttgca cttagtagcc tctcaggcga catccagaag atgaagcagc tcatgcgttt    1020
gtatcggatg aaaggagata tgcgccgta catgacatta cttggtgata gtgaccagat    1080
gagctttgcg cctgccgagt atgcacaact ttactccttt gccatgggta tggcatcagt    1140
cctagataaa ggtactggga ataccaatt tgccaggga tttatgagca catcattctg     1200
gagacttgga gtagagtacg ctcaggctca gggaagtagc attaacgagg atatggctgc    1260
cgagctaaag ctaaccccag cagcaatgaa gggcctggca gctgctgccc aacgggtctc    1320
cgacgatacc agcagcatat acatgcctac tcaacaagtc ggagtcctca ctgggcttag    1380
cgaggggggg tcccaagctc tacaaggcgg atcgaataga tcgcaagggc aaccagaagc    1440
cggggatggg gagacccaat tcctggatct gatgagagcg gtagcaaata gcatgaggga    1500
ggcgccaaac tctgcacagg gcactcccca atcggggcct cccccaactc ctgggccatc    1560
ccaagataac gacaccgact gggggtattg atggacaaaa cccagcctgc ttccacaaaa    1620
acatcccaat gccctcaccc gtagtcgacc cctcgatttg cggctctata tgaccacacc    1680
ctcaaacaaa catccccctc tttcctccct cccctgctg tacaactccg cacgccctag    1740
ataccacagg cacaatgcgg ctcactaaca atcaaaacag agccgaggga attagaaaaa    1800
agtacgggta gaagagggat attcagagat caggcaagt ctcccgagtc tctgctctct    1860
cctctacctg ataggacagg acaaacatgg ccaccttac agatgcagag atcgacgagc    1920
```

-continued

```
tatttgagac aagtggaact gtcattgaca acataattac agcccagggt aaaccagcag    1980
agactgttgg aaggagtgca atcccacaag gcaagaccaa ggtgctgagc gcagcatggg    2040
agaagcatgg gagcatccag ccaccggcca gtcaagacaa ccccgatcga caggacagat    2100
ctgacaaaca accatccaca cccgagcaaa cgaccccgca tgacagcccg ccggccacat    2160
ccgccgacca gccccccacc caggccacac acgaagccgt cgacacacag ttcaggaccg    2220
gagcaagcaa ctctctgctg ttgatgcttg acaagctcag caataaatcg tccaatgcta    2280
aaaagggccc atggtcgagc ccccaagagg ggaatcacca acgtccgact caacagcagg    2340
ggagtcaacc cagtcgcgga aacagtcagg aaagaccgca gaaccaagtc aaggccgccc    2400
ctggaaacca gggcacagac gtgaacacag catatcatgg acaatgggag gagtcacaac    2460
tatcagctgg tgcaacccct catgctctcc gatcaaggca gagccaagac aatacccttg    2520
tatctgcgga tcatgtccag ccacctgtag actttgtgca agcgatgatg tctatgatgg    2580
aggcgatatc acagagagta agtaaggttg actatcagct agatcttgtc ttgaaacaga    2640
catcctccat ccctatgatg cggtccgaaa tccaacagct gaaaacatct gttgcagtca    2700
tggaagccaa cttgggaatg atgaagattc tggatcccgg ttgtgccaac atttcatctc    2760
tgagtgatct acgggcagtt gcccgatctc acccggtttt agtttcaggc cctggagacc    2820
cctctccta tgtgacacaa ggaggcgaaa tggcacttaa taaactttcg caaccagtgc    2880
cacatccatc tgaattgatt aaacccgcca ctgcatgcgg gcctgatata ggagtggaaa    2940
aggacactgt ccgtgcattg atcatgtcac gcccaatgca cccgagttct tcagccaagc    3000
tcctaagcaa gttagatgca gccgggtcga tcgaggaaat caggaaaatc aagcgccttg    3060
ctctaaatgg ctaattacta ctgccacacg tagcgggtcc ctgtccactc ggcatcacac    3120
ggaatctgca ccgagttccc ccccgcagac ccaaggtcca actctccaag cggcaatcct    3180
ctctcgcttc ctcagcccca ctgaatggtc gcgtaaccgt aattaatcta gctacattta    3240
agattaagaa aaaatacggg tagaattgga gtgccccaat tgtgccaaga tggactcatc    3300
taggacaatt gggctgtact ttgattctgc ccattcttct agcaacctgt tagcatttcc    3360
gatcgtccta caaggcacag gagatgggaa gaagcaaatc gccccgcaat ataggatcca    3420
gcgccttgac ttgtggactg atagtaagga ggactcagta ttcatcacca cctatggatt    3480
catctttcaa gttgggaatg aagaagccac tgtcggcatg atcgatgata acccaagcg    3540
cgagttactt tccgctgcga tgctctgcct aggaagcgtc ccaaataccg agaccttat     3600
tgagctggca agggcctgtc tcactatgat agtcacatgc aagaagagtg caactaatac    3660
tgagagaatg gttttctcag tagtgcaggc accccaagtg ctgcaaagct gtagggttgt    3720
ggcaaacaaa tactcatcag tgaatgcagt caagcacgtg aaagcgccag agaagattcc    3780
cgggagtgga accctagaat acaaggtgaa cttttgtctcc ttgactgtgg taccgaagaa    3840
ggatgtctac aagatcccag ctgcagtatt gaaggtttct ggctcgagtc tgtacaatct    3900
tgcgctcaat gtcactatta atgtggaggt agacccgagg agtcctttgg ttaaatcttt    3960
gtctaagtct gacagcggat actatgctaa cctcttcttg catattggac ttatgaccac    4020
cgtagatagg aaggggaaga aagtgacatt tgacaagctg gaaaagaaaa taaggagcct    4080
tgatctatct gtcgggctca gtgatgtgct cgggccttcc gtgttggtaa aagcaagagg    4140
tgcacggact aagcttttgg cacctttctt ctctagcagt gggacagcct gctatcccat    4200
agcaaatgct tctcctcagg tggccaagat actctggagt caaaccgcgt gcctgcggag    4260
cgttaaaatc attatccaag caggtaccca acgcgctgtc gcagtgaccg ccgaccacga    4320
```

```
ggttacctct actaagctgg agaaggggca cacccttgcc aaatacaatc cttttaagaa    4380
ataagctgcg tctctgagat tgcgctccgc ccactcaccc agatcatcat gacacaaaaa    4440
actaatctgt cttgattatt tacagttagt ttacctgtct atcaagttag aaaaaacacg    4500
ggtagaagat tctggatccc ggttggcgcc ctccaggtgc aagatgggct ccagaccttc    4560
taccaagaac ccagcaccta tgatgctgac tatccgggtt gcgctggtac tgagttgcat    4620
ctgtccggca aactccattg atggcaggcc tcttgcagct gcaggaattg tggttacagg    4680
agacaaagcc gtcaacatat acacctcatc ccagacagga tcaatcatag ttaagctcct    4740
cccgaatctg cccaaggata aggaggcatg tgcgaaagcc cccttggatg catacaacag    4800
gacattgacc actttgctca cccccttgg tgactctatc cgtaggatac aagagtctgt      4860
gactacatct ggagggggga gacaggggcg cctataggc gccattattg gcggtgtggc      4920
tcttggggtt gcaactgccg cacaaataac agcggccgca gctctgatac aagccaaaca    4980
aaatgctgcc aacatcctcc gacttaaaga gagcattgcc gcaaccaatg aggctgtgca    5040
tgaggtcact gacggattat cgcaactagc agtggcagtt gggaagatgc agcagtttgt    5100
taatgaccaa tttaataaaa cagctcagga attagactgc atcaaaattg cacagcaagt    5160
tggtgtagag ctcaacctgt acctaaccga attgactaca gtattcggac cacaaatcac    5220
ttcacctgct ttaaacaagc tgactattca ggcactttac aatctagctg gtggaaatat    5280
ggattactta ttgactaagt taggtgtagg gaacaatcaa ctcagctcat taatcggtag    5340
cggcttaatc accggtaacc ctattctata cgactcacag actcaactct ggggtataca    5400
ggtaactcta ccttcagtcg ggaacctaaa taatatgcgt gccacctact tggaaaccctt   5460 atccgtaagc acaaccaggg gatttgcctc ggcacttgtc cccaaagtgg tgacacaggt    5520
cggttctgtg atagaagaac ttgacacctc atactgtata gaaactgact tagatttata    5580
ttgtacaaga atagtaacgt tccctatgtc ccctggtatt tattcctgct tgagcggcaa    5640
tacgtcggcc tgtatgtact caaagaccga aggcgcactt actacaccat acatgactat    5700
caaaggttca gtcatcgcca actgcaagat gacaacatgt agatgtgtaa acccccccggg   5760 tatcatatcg caaaactatg gagaagccgt gtctctaata gataaacaat catgcaatgt    5820
tttatcctta ggcgggataa ctttaaggct cagtggggaa ttcgatgtaa cttatcagaa    5880
gaatatctca atacaagatt ctcaagtaat aataacaggc aatcttgata tctcaactga    5940
gcttgggaat gtcaacaact cgatcagtaa tgctttgaat aagttagagg aaagcaacag    6000
aaaactagac aaagtcaatg tcaaactgac tagcacatct gctctcatta cctatatcgt    6060
tttgactatc atatctcttg tttttggtat acttagcctg attctagcat gctacctaat    6120
gtacaagcaa aaggcgcaac aaaagacctt attatggctt gggaataata ctctagatca    6180
gatgagagcc actacaaaaa tgtgaacaca gatgaggaac gaaggtttcc ctaatagtaa    6240
tttgtgtgaa agttctggta gtctgtcagt tcagagagtt aagaaaaaac taccggttgt    6300
agatgaccaa aggacgatat acgggtagaa cggtaagaga ggccgcccct caattgcgag    6360
ccaggcttca caacctccgt tctaccgctt caccgacaac agtcctcaat catggaccgc    6420
gccgttagcc aagttgcgtt agagaatgat gaaagagagg caaaaaatac atggcgcttg    6480
atattccgga ttgcaatctt attcttaaca gtagtgacct tggctatatc tgtagcctcc    6540 ctttttatata gcatggggc tagcacacct agcgatcttg taggcatacc gactaggatt    6600
tccagggcag aagaaaagat tacatctaca cttggttcca atcaagatgt agtagatagg    6660
```

-continued

```
atatataagc aagtggccct tgagtctccg ttggcattgt taaatactga gaccacaatt    6720
atgaacgcaa taacatctct ctcttatcag attaatggag ctgcaaacaa cagtgggtgg    6780
ggggcaccta tccatgaccc agattatata gggggatag gcaaagaact cattgtagat     6840
gatgctagtg atgtcacatc attctatccc tctgcatttc aagaacatct gaattttatc    6900
ccggcgccta ctacaggatc aggttgcact cgaatacct catttgacat gagtgctacc     6960
cattactgct acacccataa tgtaatattg tctggatgca gagatcactc acattcatat    7020
cagtatttag cacttggtgt gctccggaca tctgcaacag ggagggtatt cttttctact    7080
ctgcgttcca tcaacctgga cgacacccaa atcggaagt cttgcagtgt gagtgcaact     7140
cccctgggtt gtgatatgct gtgctcgaaa gtcacggaga cagaggaaga agattataac   7200
tcagctgtcc ctacgcggat ggtacatggg aggttagggt tcgacggcca gtaccacgaa   7260
aaggacctag atgtcacaac attattcggg gactgggtgg ccaactaccc aggagtaggg    7320
ggtggatctt ttattgacag ccgcgtatgg ttctcagtct acggagggtt aaaacccaat    7380
tcacccagtg acactgtaca ggaagggaaa tatgtgatat acaagcgata caatgacaca   7440
tgcccagatg agcaagacta ccagattcga atggccaagt cttcgtataa gcctggacgg   7500
tttggtggga aacgcataca gcaggctatc ttatctatca aggtgtcaac atccttaggc    7560
gaagacccgg tactgactgt accgcccaac acagtcacac tcatggggc cgaaggcaga    7620 attctcacag tagggacatc tcatttcttg tatcaacgag ggtcatcata cttctctccc    7680
gcgttattat atcctatgac agtcagcaac aaaacagcca ctcttcatag tccttataca    7740
ttcaatgcct tcactcggcc aggtagtatc ccttgccagg cttcagcaag atgccccaac    7800
tcgtgtgtta ctggagtcta tacagatcca tatccctaa tcttctatag aaaccacacc    7860
ttgcgagggg tattcgggac aatgcttgat ggtgtacaag caagacttaa ccctgcgtct    7920
gcagtattcg atagcacatc ccgcagtcgc attactcgag tgagttcaag cagtaccaaa    7980
gcagcataca caacatcaac ttgttttaaa gtggtcaaga ctaataagac ctattgtctc    8040
agcattgctg aaatatctaa tactctcttc ggagaattca gaatcgtccc gttactagtt   8100
gagatcctca aagatgacgg ggttagagaa gccaggtctg gctagttgag tcaattataa   8160
aggagttgga aagatggcat tgtatcacct atcttctgcg acatcaagaa tcaaaccgaa    8220
tgccggcgcg tgctcgaatt ccatgttgcc agttgaccac aatcagccag tgctcatgcg    8280
atcagattaa gccttgtcat taatctcttg attaagaaaa aatgtaagtg gcaatgagat    8340
acaaggcaaa acagctcatg gtaaataata cgggtaggac atggcgagct ccggtcctga    8400
aagggcagag catcagatta tcctaccaga gccacacctg tcttcaccat tggtcaagca    8460
caaactactc tattactgga aattaactgg gctaccgctt cctgatgaat gtgacttcga    8520
ccacctcatt ctcagccgac aatggaaaaa aatacttgaa tcggcctctc ctgatactga    8580
gagaatgata aaactcggaa gggcagtaca ccaaactctt aaccacaatt ccagaataac    8640
cggagtgctc caccccaggt gtttagaaca actggctaat attgaggtcc cagattcaac    8700
caacaaattt cggaagattg agaagaagat ccaaattcac aacacgagat atggagaact    8760
gttcacaagg ctgtgtacgc atatagagaa gaaactgctg gggtcatctt ggtctaacaa    8820
tgtcccccgg tcagaggagt tcagcagcat tcgtacggat ccggcattct ggtttcactc    8880
aaaatggtcc acagccaagt ttgcatggct ccatataaaa cagatccaga ggcatctgat    8940
ggtggcagct aagacaaggt ctgcggccaa caaattggtg atgctaaccc ataaggtagg    9000
ccaagtcttt gtcactcctg aacttgtcgt tgtgacgcat acgaatgaga acaagttcac    9060
```

```
atgtcttacc caggaacttg tattgatgta tgcagatatg atggagggca gagatatggt   9120
caacataata tcaaccacgg cggtgcatct cagaagctta tcagagaaaa ttgatgacat   9180
tttgcggtta atagacgctc tggcaaaaga cttgggtaat caagtctacg atgttgtatc   9240
actaatggag ggatttgcat acggagctgt ccagctactc gagccgtcag gtacatttgc   9300
aggagatttc ttcgcattca acctgcagga gcttaaagac attctaattg gcctcctccc   9360
caatgatata gcagaatccg tgactcatgc aatcgctact gtattctctg gtttagaaca   9420
gaatcaagca gctgagatgt tgtgtctgtt gcgtctgtgg ggtcacccac tgcttgagtc   9480
ccgtattgca gcaaaggcag tcaggagcca aatgtgcgca ccgaaaatgg tagactttga   9540
tatgatcctt caggtactgt ctttcttcaa gggaacaatc atcaacgggt acagaaagaa   9600
gaatgcaggt gtgtggccgc gagtcaaagt ggatacaata tatgggaagg tcattgggca   9660
actacatgca gattcagcag agatttcaca cgatatcatg ttgagagagt ataagagttt   9720
atctgcactt gaatttgagc catgtataga atatgaccct gtcaccaacc tgagcatgtt   9780
cctaaaagac aaggcaatcg cacaccccaa cgataattgg cttgcctcgt ttaggcggaa   9840
ccttctctcc gaagaccaga agaaacatgt aaaagaagca acttcgacta atcgcctctt   9900
gatagagttt ttagagtcaa atgattttga tccatataaa gagatggaat atctgacgac   9960
ccttgagtac cttagagatg acaatgtggc agtatcatac tcgctcaagg agaaggaagt  10020
gaaagttaat ggacggatct tcgctaagct gacaaagaag ttaaggaact gtcaggtgat  10080
ggcggaaggg atcctagccg atcagattgc accttctctt cagggaaatg gagtcattca  10140
ggatagcata tccttgacca agagtatgct agcgatgagt caactgtctt ttaacagcaa  10200
taagaaacgt atcactgact gtaaagaaag agtatcttca aaccgcaatc atgatccgaa  10260
aagcaagaac cgtcggagag ttgcaacctt cataacaact gacctgcaaa agtactgtct  10320
taattggaga tatcagacaa tcaaattgtt cgctcatgcc atcaatcagt tgatgggcct  10380
acctcacttc ttcgaatgga ttcacctaag actgatggac actacgatgt tcgtaggaga  10440
cccttttcaat cctccaagtg accctactga ctgtgacctc tcaagagtcc ctaatgatga  10500
catatatatt gtcagtgcca gagggggtat cgaaggatta tgccagaagc tatggacaat  10560
gatctcaatt gctgcaatcc aacttgctgc agctagatcg cattgtcgtg ttgcctgtat  10620
ggtacagggt gataatcaag taatagcagt aacgagagag gtaagatcag acgactctcc  10680
ggagatggtg ttgacacagt tgcatcaagc cagtgataat ttcttcaagg aattaattca  10740
tgtcaatcat ttgattggcc ataatttgaa ggatcgtgaa accatcaggt cagacacatt  10800
cttcatatac agcaaacgaa tcttcaaaga tggagcaatc ctcagtcaag tcctcaaaaa  10860
ttcatctaaa ttagtgctag tgtcaggtga tctcagtgaa acaccgtaa tgtcctgtgc  10920
caacattgcc tctactgtag cacggctatg cgagaacggg cttcccaaag acttctgtta  10980
ctatttaaac tatataatga gttgtgtgca gacatacttt gactctgagt tctccatcac  11040
caacaattcg cacccccgatc ttaatcagtc gtggattgag acatctcttt tgtgcactc  11100
atatgttctg actcctgccc aattagggg actgagtaac cttcaatact caaggctcta  11160
cactagaaat atcggtgacc cggggactac tgcttttgca gagatcaagc gactagaagc  11220
agtgggatta ctgagtccta acattatgac taatatctta actaggccgc tgggaatgg  11280
agattgggcc agtctgtgca acgacccata ctctttcaat tttgagactg ttgcaagccc  11340
aaatattgtt cttaagaaac atacgcaaag agtcctattt gaaacttgtt caaatccctt  11400
```

```
attgtctgga gtgcacacag aggataatga ggcagaagag aaggcattgg ctgaattctt    11460
gcttaatcaa gaggtgattc atccccgcgt tgcgcatgcc atcatggagg caagctctgt    11520
aggtaggaga aagcaaattc aagggcttgt tgacacaaca aacaccgtaa ttaagattgc    11580
gcttactagg aggccattag gcatcaagag gctgatgcgg atagtcaatt attctagcat    11640
gcatgcaatg ctgtttagag acgatgtttt ttcctccagt agatccaacc accccttagt    11700
ctcttctaat atgtgttctc tgacactggc agactatgca cggaatagaa gctggtcacc    11760
tttgacggga ggcaggaaaa tactgggtgt atctaatcct gatacgatag aactcgtaga    11820
gggtgagatt cttagtgtaa gcggagggtg tacaagatgt gacagcggag atgaacaatt    11880
tacttggttc catcttccaa gcaatataga attgaccgat gacaccagca agaatcctcc    11940
gatgagggta ccatatctcg ggtcaaagac acaggagagg agagctgcct cacttgcaaa    12000
aatagctcat atgtcgccac atgtaaaggc tgccctaagg gcatcatccg tgttgatctg    12060
ggcttatggg gataatgaag taaattggac tgctgctctt acgattgcaa aatctcggtg    12120
taatgtaaac ttagagtatc ttcggttact gtccccttta cccacggctg ggaatcttca    12180
acatagacta gatgatggta taactcagat gacattcacc cctgcatctc tctacaggtg    12240
tcaccttaca ttcacatatc aatgattct caaaggctgt tcactgaaga aggagtcaaa    12300
gaggggaatg tggtttacca acagagtcat gctcttgggt ttatctctaa tcgaatcgat    12360
ctttccaatg acaacaacca ggacatatga tgagatcaca ctgcacctac atagtaaatt    12420
tagttgctgt atcagagaag cacctgttgc ggttcctttc gagctacttg gggtggtacc    12480
ggaactgagg acagtgacct caaataagtt tatgtatgat cctagccctg tatcggaggg    12540
agactttgcg agacttgact tagctatctt caagagttat gagcttaatc tggagtcata    12600
tcccacgata gagctaatga acattctttc aatatccagc gggaagttga ttggccagtc    12660
tgtggttct tatgatgaag atacctccat aaagaatgac gccataatag tgtatgacaa    12720
tacccgaaat tggatcagtg aagctcagaa ttcagatgtg gtccgcctat ttgaatatgc    12780
agcacttgaa gtgctcctcg actgttctta ccaactctat tacctgagag taagaggcct    12840
agacaatatt gtcttatata tgggtgattt atacaagaat atgccaggaa ttctactttc    12900
caacattgca gctacaatat ctcatcccgt cattcattca aggttacatg cagtgggcct    12960
ggtcaaccat gacggatcac accaacttgc agatacggat tttatcgaaa tgtctgcaaa    13020
actattagta tcttgcaccc gacgtgtgat ctccggctta tattcaggaa ataagtatga    13080
tctgctgttc ccatctgtct tagatgataa cctgaatgag aagatgcttc agctgatatc    13140
ccggttatgc tgtctgtaca cggtactctt tgctacaaca agagaaatcc cgaaaataag    13200
aggcttaact gcagaagaga aatgttcaat actcactgag tatttactgt cggatgctgt    13260
gaaaccatta cttagccccg atcaagtgag ctctatcatg tctcctaaca taattacatt    13320
cccagctaat ctgtactaca tgtctcggaa gagcctcaat ttgatcaggg aaagggagga    13380
cagggatact atcctggcgt tgttgttccc ccaagagcca ttattagagt tcccttctgt    13440
gcaagatatt ggtgctcgag tgaaagatcc attcacccga caacctgcgg cattttttgca    13500
agagttagat ttgagtgctc cagcaaggta tgacgcattc acacttagtc agattcatcc    13560
tgaactcaca tctccaaatc cggaggaaga ctacttagta cgatacttgt tcagagggat    13620
agggactgca tcttcctctt ggtataaggc atctcatctc ctttctgtac ccgaggtaag    13680
atgtgcaaga cacgggaact ccttatactt agctgaaggg agcggagcca tcatgagtct    13740
tctcgaactg catgtaccac atgaaactat ctattacaat acgctctttt caaatgagat    13800
```

-continued

| | |
|---|---|
| gaaccccccg caacgacatt tcgggccgac cccaactcag ttttttgaatt cggttgttta | 13860 |
| taggaatcta caggcggagg taacatgcaa agatggattt gtccaagagt tccgtccatt | 13920 |
| atggagagaa aatacagagg aaagtgacct gacctcagat aaagcagtgg ggtatattac | 13980 |
| atctgcagtg ccctacagat ctgtatcatt gctgcattgt gacattgaaa ttcctccagg | 14040 |
| gtccaatcaa agcttactag atcaactagc tatcaattta tctctgattg ccatgcattc | 14100 |
| tgtaagggag ggcggggtag taatcatcaa agtgttgtat gcaatgggat actactttca | 14160 |
| tctactcatg aacttgtttg ctccgtgttc cacaaaagga tatattctct ctaatggtta | 14220 |
| tgcatgtcga ggagatatgg agtgttacct ggtatttgtc atgggttacc tgggcgggcc | 14280 |
| tacatttgta catgaggtgg tgaggatggc aaaaactctg gtgcagcggc acggtacgct | 14340 |
| cttgtctaaa tcagatgaga tcacactgac caggttattc acctcacagc ggcagcgtgt | 14400 |
| gacagacatc ctatccagtc ctttaccaag attaataaag tacttgagga agaatattga | 14460 |
| cactgcgctg attgaagccg ggggacagcc cgtccgtcca ttctgtgcgg agagtctggt | 14520 |
| gagcacgcta gcgaacataa ctcagataac ccagattatc gctagtcaca ttgacacagt | 14580 |
| tatccggtct gtgatatata tggaagctga gggtgatctc gctgacacag tatttctatt | 14640 |
| tacccccttac aatctctcta ctgacggaa aaagaggaca tcacttatac agtgcacgag | 14700 |
| acagatccta gaggttacaa tactaggtct tagagtcgaa atctcaata aaataggcga | 14760 |
| tataatcagc ctagtgctta aaggcatgat ctccatggag gacctatacc cactaaggac | 14820 |
| atacttgaag catagtacct gccctaaata tttgaaggct gtcctaggta ttaccaaact | 14880 |
| caaagaaatg tttacagaca cttctgtatt gtacttgact cgtgctcaac aaaaattcta | 14940 |
| catgaaaact ataggcaatg cagtcaaagg atattacagt aactgtgact cttaacgaaa | 15000 |
| atcacatatt aataggctcc ttttttggcc aattgtattc ttgttgattt aatcatatta | 15060 |
| tgttagaaaa aagttgaacc ctgactcctt aggactcgaa ttcgaactca ataaatgtc | 15120 |
| ttaaaaaaag gttgcgcaca attattcttg agtgtagtct cgtcattcac caaatctttg | 15180 |
| tttggt | 15186 |

<210> SEQ ID NO 4
<211> LENGTH: 1611
<212> TYPE: DNA
<213> ORGANISM: infectious bronchitis virus (IBV)

<400> SEQUENCE: 4

| | |
|---|---|
| atgttggtaa cacctctttt actagtgact cttttgtgtg cactatgtag tgctgctttg | 60 |
| tatgacagta gttcttacgt gtactactac caaagtgcct tcagaccacc tgatggttgg | 120 |
| catttacatg ggggtgcgta tgcggttgtt aatatttcta gtgaatctaa taatgcaggc | 180 |
| tcttcatctg ggtgtactgt tggtattatt catggtggtc gtgttgttaa tgcttcttct | 240 |
| atagctatga cggcaccgtc atcaggtatg gcttggtcta gcagtcagtt tgtactgca | 300 |
| tactgtaact tttcagatac tacagtgttt gttacacatt gtacaaaca tgttgggtgt | 360 |
| cctataactg gcatgcttca acagcattct atacgtgttt ctgctatgaa aaatggccag | 420 |
| ctttttttata atttaacagt tagtgtagct aagtaccta cttttaaatc atttcagtgt | 480 |
| gttaataatt taacatccgt atatttaaat ggtgatcttg tttacacctc taatgagacc | 540 |
| acagatgtta catctgcagg tgtttatttt aaagctggtg gacctataac ttataaagtt | 600 |
| atgagagaag ttagagccct ggcttatttt gttaatggta ctgcacaaga tgttattttg | 660 |

| | |
|---|---|
| tgtgatgggt cacctagagg cttgttagca tgccagtata atactggcaa tttttcagat | 720 |
| ggctttatc cttttactaa tagtagttta gttaagcaga agtttattgt ctatcgtgaa | 780 |
| aatagtgtta atactacttt tacgttacac aatttcactt ttcataatga gactggcgcc | 840 |
| aacccaaatc ctagtggtgt ccagaatatt caaacttacc aaacacaaac agctcagagt | 900 |
| ggttattata attttaattt ttcctttctg agtagttttg tttataagga gtctaatttt | 960 |
| atgtatggat cttatcaccc aagttgtaat tttagactag aaactattaa taatggtttg | 1020 |
| tggtttaatt cactttcagt ttcaattgct tacggtcctc ttcaaggtgg ttgcaagcaa | 1080 |
| tctgtcttta gtggtagagc aacctgttgt tatgcttact catatggagg tcctttgctg | 1140 |
| tgtaaaggtg tttattcagg tgagttagat cataattttg aatgtggact gttagtttat | 1200 |
| gttactaaga gcggtggctc tcgtatacaa acagccactg aaccgccagt tataactcaa | 1260 |
| cacaattata ataatattac tttaaatact tgtgttgatt ataatatata tggcagaact | 1320 |
| ggccaaggtt ttattactaa tgtaaccgac tcagctgtta gttataatta ctagcagac | 1380 |
| gcaggtttgg ctattttaga tacatctggt tccatagaca tctttgtcgt acaaagtgaa | 1440 |
| tatggtctta attattataa ggttaaccct tgcgaagatg tcaaccagca gtttgtagtt | 1500 |
| tctggtggta aattagtagg tattcttact tcacgtaatg agactggttc ccagcttctt | 1560 |
| gagaatcagt tttacatcaa aatcactaat ggaacacgtc gttttagacg t | 1611 |

<210> SEQ ID NO 5
<211> LENGTH: 960
<212> TYPE: DNA
<213> ORGANISM: infectious laryngotracheitis virus (ILTV)

<400> SEQUENCE: 5

| | |
|---|---|
| ggagggaga gagacaactt cagctcgaag tctgaagaga catcatgagc ggcttcagta | 60 |
| acataggatc gattgccacc gtttccctag tatgctcgct tttgtgcgca tctgtattag | 120 |
| gggcgccggt actggacggg ctcgagtcga gcccttttccc gttcgggggc aaaattatag | 180 |
| cccaggcgtg caaccgcacc acgattgagg tgacggtccc gtggagcgac tactctggtc | 240 |
| gcaccgaagg agtgtcagtc gaggtgaaat ggttctacgg gaatagtaat cccgaaagct | 300 |
| tcgtgttcgg ggtggatagc gaaacgggca gtggacacga ggacctgtct acgtgctggg | 360 |
| ctctaatcca taatctgaac gcgtctgtgt gcaggcgtc tgacgccggg ataccctgatt | 420 |
| tcgacaagca gtgcgaaaaa gtgcagaaga gactgcgctc cggggtggaa cttggtagtt | 480 |
| acgtgtctgg caatggatcc ctggtgctgt acccagggat gtacgatgcc ggcatctacg | 540 |
| cctaccagct ctcagtgggt gggaagggat ataccgggtc tgtttatcta gacgtcggac | 600 |
| caaaccccgg atgccacgac cagtatgggt acacctatta cagcctggcc gacgaggcgt | 660 |
| cagacttatc atcttatgac gtagcctcgc ccgaactcga cggtcctatg gaggaagatt | 720 |
| attccaattg tctagacatg cccccgctac gcccatggac aaccgttttgt tcgcatgacg | 780 |
| tcgaggagca ggaaaacgcc acggacgagc tttacctatg ggacgaggaa tgcgccggtc | 840 |
| cgctggacga gtacgtcgac gaaaggtcag agacgatgcc caggatggtt gtcttttcac | 900 |
| cgccctctac gctccagcag tagccacccg agagtgtttt ttgtgagcgc ccacgcaaca | 960 |

<210> SEQ ID NO 6
<211> LENGTH: 810
<212> TYPE: DNA
<213> ORGANISM: avian encephalomyelitis virus (AEV)

<400> SEQUENCE: 6

```
gggaaagagg atgaaggagg attttttcagt gtgcctgaag tggagcaaca tgttgttgag      60
gataaggaac cacagggacc tttgcacgtg acaccttttg gcgctgttaa agctatggag     120 gaccccccaat tggccaggaa aacacctggc acattccctg aattagctcc tggtaaacct    180
cgacatacag tggaccacat ggatctgtat aagttcatgg ggcgtgccca ttacttgtgg     240
ggacatgaat tcaccaaaac tgacatgcag tacacattcc agataccatt aagtcccatt     300
aaagagggtt ttgtgacggg tacacttagg tggttttaa gtcttttcca actgtatcgt     360
ggttctctcg acattaccat gacatttgca ggaaaaacta atgtggatgg cattgtgtac     420
tttgtgcctg agggtgttgc gatagagact gagagggagg agcagacccc tttgctcaca     480
ttgaactata aaacatcggt aggtgccatt aggtttaata ctggacaaac tacgaatgtc     540
cagtttagga tcccttttcta cacgccactg gaacacatcg caacccattc taaaaatgcg    600
atggattcag tcttggggggc aatcacaacc cagatcacta actatagtgc tcaggatgag    660
tatttgcagg ttacctacta catcagtttc aatgaagatt cacagttttc tgttcccaga     720
gcggtgccag tggtcagctc attcactgac acatctagca aaacagtgat gaatacatat     780
tggcttgatg atgacgagtt ggtagaagag                                       810

<210> SEQ ID NO 7
<211> LENGTH: 726
<212> TYPE: DNA
<213> ORGANISM: avian encephalomyelitis virus (AEV)

<400> SEQUENCE: 7
atgagcaaac tattttctac tgtaggcagg actgttgatg aggttttgtc tgtgctcaat      60
gatgaggata ctgaatctta tgctggccct gatcgcactg cagtagttgg cggaggattt     120
ctgacaacgg tagaccagag ttcagttagc acggctacaa tgggaagttt acaagatgta     180
cagtacagga ctgcagtcga tattcctggt tctagagtga cacaaggtga gaggttcttc     240
cttatcgatc agcgtgagtg gaactcaaca cagagtgaat ggcagttatt gggcaagatt     300
gacatagtaa aagagctgct tgatcagtcg tatgctgttg atggccttttt gaagtaccat    360 tcttatgcaa ggtttggctt ggatgtcatt gttcagatta atccaacatc attccaggca     420
gggggcctca tagcagctct cgtacccttat gaccaggttg acattgaatc aattgttgcc    480
atgaccactt attgccatgg caaggttaat tgcaacataa actacgttgt aaggatgaag     540
gtgccatata tatacagtcg aggttgttac aaccttagga actcagcata ctccatttgg     600
atgcttgtga taagagtgtg gtcacggctg cagttgggat ctggcacttc aacacagatt     660
actatcacca ccttggctag gtttgtggat ttggaactgc atggacttag ccctttggtc     720
gcacag                                                                 726

<210> SEQ ID NO 8
<211> LENGTH: 735
<212> TYPE: DNA
<213> ORGANISM: avian encephalomyelitis virus (AEV)

<400> SEQUENCE: 8
atgatgcgca acgaatttcg actgtcgtca tctagcaaca ttgtcaattt ggctaattat      60
gacgatgcaa gagccaaagt gtctctagcg ctgggacaag aagagtttttc cagagactcg    120 tcaagtaccg ggggggaatt ggtgcatcat ttttcacagt ggacgtccat tccgtgcctt     180
gccttcactt ttacattccc cggcacggta gggccaggca ctcacatctg gtcaaccacg     240
```

-continued

```
gtggacccctt tttcctgtaa cttgagggcg tctagcactg tgcaccccac taacttgagc    300
tcgattgcgg gtatgttctg tttttggaga ggtgacattg tatttgagtt tcaagtcttt    360
tgcaccaagt atcattccgg caggttgatg tttgtgtatg tgcctggcga tgaaaacaca    420
aaaatcagca ccttaactgc aaaacaagca tctactggtc ttactgctgt ttttgatatc    480
aatggtgtaa attcaacact ggtgtttaga tgccctttca tctctgacac accttacagg    540
gtgaatccaa cgactcataa gtccctctgg ccttatgcaa ctggcaagct tgtgtgctat    600
gtctacaata tactgaacgc acctgccagt gtatcaccaa ccctgcccat taatgtgtac    660
aaaagtgctg cggatctgga gttgtatgca cctgtttatg ggtttctcc caccaacacc    720 tcaattttg ttcaa                                                       735

<210> SEQ ID NO 9
<211> LENGTH: 1500
<212> TYPE: DNA
<213> ORGANISM: avian parainfluenza virus (APV)

<400> SEQUENCE: 9
ggggggtgtg catggtaggg tggggaaggt agccaattcc tgcccattgg gccgaccgta     60
ccaagagaag tcaacagaag tatagatgca gggcgacatg gagggtagcc gtgataacct    120
cacagtagat gatgaattaa agacaacatg gaggttagct tatagagttg tatccctcct    180
attgatggtg agtgccttga taatctctat agtaatcctg acgagagata acagccaaag    240
cataatcacg gcgatcaacc agtcgtatga cgcagactca aagtggcaaa cagggataga    300
agggaaaatc acctcaatca tgactgatac gctcgatacc aggaatgcag ctcttctcca    360
cattccactc cagctcaata cacttgaggc aaacctgttg tccgccctcg gaggttacac    420
gggaattggc cccggagatc tagagcactg tcgttatccg gttcatgact ccgcttacct    480
gcatggagtc aatcgattac tcatcaatca aacagctgac tacacagcag aaggccccct    540
ggatcatgtg aacttcattc cggcaccagt tacgactact ggatgcacaa ggatcccatc    600
cttttctgta tcatcatcca tttggtgcta tacacacaat gtgattgaaa caggttgcaa    660
tgaccactca ggtagtaatc aatatatcag tatgggggtg attaagaggg ctggcaacgg    720
cttaccttac ttctcaacag tcgtgagtaa gtatctgacc gatgggttga atagaaaaag    780
ctgttccgta gctgcgggat ccgggcattg ttacctcctt tgtagcctag tgtcagagcc    840
cgaacctgat gactatgtgt caccagatcc cacaccgatg aggttagggg tgctaacaag    900
ggatgggtct tacactgaac aggtggtacc cgaaagaata tttaagaaca tatggagcgc    960 aaactacccct ggggtagggt caggtgctat agcaggaaat aaggtgttat tcccattta   1020 cggcggagtg aagaatggat caaccccctga ggtgatgaat aggggaagat attactacat   1080
ccaggatcca aatgactatt gccctgaccc gctgcaagat cagatcttaa gggcagaaca   1140
atcgtattat cctactcgat ttggtaggag atggtaatg cagggagtcc taacatgtcc   1200
agtatccaac aattcaacaa tagccagcca atgccaatct tactatttca caactcatt   1260 aggattcatc ggggcggaat ctaggatcta ttacctcaat ggtaacattt accttttatca   1320 aagaagctcg agctggtggc ctcaccccca aatttaccta cttgattcca ggattgcaag   1380
tccgggtacg cagaacattg actcaggcgt taacctcaag atgttaaatg ttactgtcat   1440
tacacgacca tcatctggct tttgtaatag tcagtcaaga tgccctaatg actgcttatt   1500

<210> SEQ ID NO 10
<211> LENGTH: 1440
```

-continued

<212> TYPE: DNA
<213> ORGANISM: hemorrhagic enteritis virus (HEV)

<400> SEQUENCE: 10

| | | | | | |
|---|---|---|---|---|---|
| gaaatgttaa | tgttagacca | tactgaccaa | ttcctggttc | attttagatg | gaatcttcga | 60 |
| acactgccac | tagaattttt | gctccaacgg | aagggagaaa | cagtataatt | tacagcaact | 120 |
| tgcctcctgt | tcaagataca | accaaaatat | tttatataga | taacaaggcc | attgatatag | 180 |
| agtcatataa | tcaagagaaa | gatcattcta | attattatac | taatataatt | caaacacaga | 240 |
| acatttcaac | tattgattca | agtatacagc | aaattcagtt | agatgaaagg | tctagatggg | 300 |
| gaggagaact | acatacaagc | ttagtaacat | ctgttatgaa | ttgtactaaa | cattttaatt | 360 |
| cagataggtg | tttagtgaaa | attcagacta | ttaagagtcc | acctacattt | gaatggaaag | 420 |
| aattgaaaat | acctgaggga | actatgtttt | aaatgagtt | tattgattta | ttaaatgaag | 480 |
| gtattacttc | tttataccctt | cagtatggca | ggcaacaggg | tgtacttgaa | gaagacatag | 540 |
| gaataaaatt | tgatactcgc | aattttgaaa | ttggtaaaga | tccaactact | aatcttgtta | 600 |
| ctcctggtaa | atacttgttt | aagggttatc | atgctgatat | aatacttctt | cctggttggg | 660 |
| ctattgattt | ttctttttct | agattgggta | acattttagg | tattagaaaa | cgtgagactt | 720 |
| ataaagctgg | ctttttgatt | gaatatgatg | acttgacaaa | tggtaatatt | ccaccactgt | 780 |
| tggatgttgc | taactataag | tctacaagtc | aagctaaacc | attattacag | gatccatctg | 840 |
| gcagatctta | ccacgttatg | gatagtgatt | ctaacagacc | tgtgactgca | tataggtctt | 900 |
| ttgttttgtc | atataacaat | gaaggtgctg | caaaattaaa | gttttttgatg | tgtatgagtg | 960 |
| atataacggg | gggtctcaat | cagctgtatt | ggtgtttgcc | tgattcttat | aaaccgccag | 1020 |
| tatcttttaa | gcaagaaacg | caagtagata | aactgcctgt | tgttggtatg | caactttttt | 1080 |
| tccttttttgt | ttgtaaatct | gtgtattctg | gtgctgctgt | ttacacacag | ttaattgaac | 1140 |
| agcagactaa | tttgacacaa | atttttaaca | gatttcatga | taatgaaatt | ttaaaacaag | 1200 |
| ctccatatgt | gaatcaagtt | ttattggctg | aaaatgtgcc | cataaatgtt | aatcagggaa | 1260 |
| caataccaat | attttcaact | cttccaggag | tacagagagt | ggttgtggaa | gacgatagga | 1320 |
| gaagaactgt | accctacgtt | accaagtcac | ttgctacagt | atatccgaag | gttttgtcta | 1380 |
| gcaaaacttt | gcaataatgc | attctgttgt | ttattctcca | ggggacagta | gaggatgggg | 1440 |

<210> SEQ ID NO 11
<211> LENGTH: 2995
<212> TYPE: DNA
<213> ORGANISM: fowlpox virus (FPV)

<400> SEQUENCE: 11

| | | | | | |
|---|---|---|---|---|---|
| ctcttaattc | gtttcaaaaa | tgggaaatat | ttttaagcct | attccaaagg | ccgattatca | 60 |
| gattgtggaa | acagtaccac | aaagcttaac | agctattaat | tctactaatc | tttctactta | 120 |
| tgaatgtttt | aaacgtttaa | tagatctagc | aaaaaaagag | atctacatag | ctacgttttg | 180 |
| ttgtaacccta | agtactaatc | ctgagggtac | tgacatacta | aacagattaa | tcgatgtttc | 240 |
| gagtaaagtt | tctgtatata | ttttagtaga | tgagagcagt | cctcataaag | attatgaaaa | 300 |
| gattaagtct | tcccatatta | gttatattaa | agtagatata | ggtgtgctta | ataatgaatc | 360 |
| agtaggaaac | ttgttaggta | atttctgggt | agtggataag | cttcactttt | atataggtag | 420 |
| tgcgtctctt | atgggaaatg | cgctaacaac | tattaaaaat | atgggcatat | attccgaaaa | 480 |
| taattccttta | gcaatggatt | tatatttcag | atcgttggac | tataaaaatta | taagcaagaa | 540 |

```
aaaatgttta ttctttacca gaatggccac aaagtaccat ttcttcaaaa accataacgg    600
tatattcttt tcagattctc cagaacatat ggtaggtaga aaaagaactt ttgacttgga    660
ttgtgttatt cattatatag acgcggcgaa gtctactata gatctagcga tagtatctct    720
tcttcctaca aagagaacaa aagattctat cgtctattgg cctataataa aagatgcatt    780
aatacgggcc gtattagaac gaggtgtcaa actacgagtg ctattaggat tttggaaaaa    840
aacggatgtt atatcaaaag catctataaa aagccttaac gaactaggag ttgaccatat    900
agatatctct actaaagtat ttaggttttcc cgttaattct aaagtagatg atattaataa    960
ttctaaaatg atgattatag atggaaggta tgctcatgtt atgactgcta acctagacgg   1020
gtctcatttt aatcaccatg cttttgttag ctttaactgt atggatcaac aatttacaaa   1080
gaaaatagct gaagtgtttg aaagggactg gatatctcct tacgcaaaag aaatagatat   1140
gtctcaaata tagtatatat gataaaaaga tcctaataaa taaatatagc atggcactaa   1200
tagaacagtt acaatcttct gaacaatcaa tactttcacc gtttagatat tatggtttta   1260
aagattttca taatgtaatt tttaccacaa tagatgacga acattaata gtaattacag    1320 tcaacaatgt accattagta actaggttaa taacgtttga aaaaataaca ttttttagat   1380
cgtttaatag tacttgtatt ataacttcca acaataattc ggatattgat acagatactt   1440 atttttatacc aaattcgtta tcactactag atattttgaa gaaaagagca tatgatgtag   1500
aactaagaga tctatcattt gctataatgt cggaaatgaa taacgatgaa ttgagaaata   1560
gtgatattgt atctctaaac aaatggctac ataagcataa tttactagac tacaaaattag  1620 tactaataag tgatatcgat agaagatata aattatacaa taaaaaaaat acaataattg   1680
atgttatatc cgtaaatggt agaaattata atatatgggt taaagatgtt atagaatatt   1740
attcaccgga atacttaaga tggtctatag atattaaaag agccacagaa agtaataact   1800
ggttaccgta tagccagtct ataaaccctt tgaatgaaaa tatatacgct tttgaattta   1860
tagctacttt agaaagatcc aatgagcgct taaatatcgg agcgatattc ctgtatccgg   1920
atataataat tacaggtaga aacaacgaag atataataga aaagttttta gatcagttag   1980
aagaagtaat atataaaaaa aattctgata gtattgtttt aacaggttat catctaacat   2040
ttttagagaa tactattta gagagatata tcagtaagta taaagactgg atttttacat    2100
gtaatcgtct agtacattgt aaaaccggca ctgaagtatt cttatttgat gccgctatat   2160
tttttccatc ctctaataag aaaggatatg taaaacattg gacaggtaaa aaattaaatt   2220
ttaaaaactt tttccaaaaa gatagtcagc tagaaaaata cataaataat aacagtgtag   2280
cagaacgtat atattattta cagtcttctt tacacaagca tatatcctgt ctaatagaaa   2340
ttttcgagtt aaatggattt gatttttaatt tttctgggtt gttagatata cttattttca   2400
gtattcgtgt taagaataat aatggtaatt actattaccc taaacattct tcagctgtga   2460
atttgatgtt gtcatctatt tacacggact attatgctat tgatgatata gataaagata   2520
gtaagaaact tgttttttaac tctatttttc ctttaataat ggaaggatat taccctgaag   2580 gaaaaccatta ttatacgaaa acacccaaag aagggtattt gtcaatatgt ttatgtgatg   2640
tagaaatatc taatgatata aagaatccta tattgtattg taaagaaaac aagtcagcta   2700
ggaagtttac aggagtattc acatctgtag atatagatac cgctgtaaaa ctaagaggat   2760
ataaaattaa aatattagaa tgtattgaat ggcctaataa aataaaatta ttcgacaata   2820
tatgttatct gaataaatta tttatagaac atcaggatta cacacacgat gaaaaatctt   2880
tacaaggcta tcttttttct tatttactta aaggcaacgt taccgaagat gttttagcta   2940
```
tgaaaagttg tagaaataat ctttctataa tatcatttat aataagttac tgcag     2995

<210> SEQ ID NO 12
<211> LENGTH: 35
<212> TYPE: DNA
<213> ORGANISM: artificial sequence
<220> FEATURE:
<223> OTHER INFORMATION: PCR primer, IBS1F'

<400> SEQUENCE: 12
cgggatccgc cgccgccatg ttggtaacac ctctt     35

<210> SEQ ID NO 13
<211> LENGTH: 29
<212> TYPE: DNA
<213> ORGANISM: artificial sequence
<220> FEATURE:
<223> OTHER INFORMATION: PCR primer, IBS1R'

<400> SEQUENCE: 13
cggaattctt aacgtctaaa acgacgtgt     29

<210> SEQ ID NO 14
<211> LENGTH: 38
<212> TYPE: DNA
<213> ORGANISM: artificial sequence
<220> FEATURE:
<223> OTHER INFORMATION: PCR primer, NDF F'

<400> SEQUENCE: 14
cgggatccgc cgccgccatg ggctccagac cttctacc     38

<210> SEQ ID NO 15
<211> LENGTH: 34
<212> TYPE: DNA
<213> ORGANISM: artificial sequence
<220> FEATURE:
<223> OTHER INFORMATION: PCR primer, NDF R'

<400> SEQUENCE: 15
ccgctcgagt tacatttttg tagtggctct catt     34

<210> SEQ ID NO 16
<211> LENGTH: 39
<212> TYPE: DNA
<213> ORGANISM: artificial sequence
<220> FEATURE:
<223> OTHER INFORMATION: PCR primer, NDHN F'

<400> SEQUENCE: 16
cgggatccgc cgccgccatg gaccgcgccg ttaggcaag     39

<210> SEQ ID NO 17
<211> LENGTH: 29
<212> TYPE: DNA
<213> ORGANISM: artificial sequence
<220> FEATURE:
<223> OTHER INFORMATION: PCR primer, NDHN R'

<400> SEQUENCE: 17
gctctagatt actcaactag ccagacctg     29

<210> SEQ ID NO 18
<211> LENGTH: 35
<212> TYPE: DNA

-continued

```
<213> ORGANISM: artificial sequence
<220> FEATURE:
<223> OTHER INFORMATION: PCR primer, IBDVP2F'

<400> SEQUENCE: 18
cgggatccgc cgccgccatg acaaacctgc aagat                         35

<210> SEQ ID NO 19
<211> LENGTH: 29
<212> TYPE: DNA
<213> ORGANISM: artificial sequence
<220> FEATURE:
<223> OTHER INFORMATION: PCR primer, IBDVP2R'

<400> SEQUENCE: 19
cggaattctt accttatggc ccggattat                                29
```